United States Patent
Keating et al.

(10) Patent No.: US 7,208,273 B2
(45) Date of Patent: Apr. 24, 2007

(54) COMMON POLYMORPHISM IN SCN5A IMPLICATED IN DRUG-INDUCED CARDIAC ARRHYTHMIA

(75) Inventors: Mark T. Keating, Brookline, MA (US); Igor Splawski, Dorchester, MA (US)

(73) Assignee: University of Utah Research Foundation, Salt Lake City, UT (US)

( * ) Notice: Subject to any disclaimer, the term of this patent is extended or adjusted under 35 U.S.C. 154(b) by 292 days.

(21) Appl. No.: 10/333,191

(22) PCT Filed: Jul. 19, 2001

(86) PCT No.: PCT/US01/22639

§ 371 (c)(1),
(2), (4) Date: Jun. 23, 2003

(87) PCT Pub. No.: WO02/08381

PCT Pub. Date: Jan. 31, 2002

(65) Prior Publication Data

US 2003/0235838 A1  Dec. 25, 2003

Related U.S. Application Data

(60) Provisional application No. 60/219,738, filed on Jul. 20, 2000.

(51) Int. Cl.
- C12Q 1/68 (2006.01)
- C07H 21/04 (2006.01)
- C12N 5/08 (2006.01)
- C12N 15/12 (2006.01)
- C07K 14/47 (2006.01)

(52) U.S. Cl. .................. 435/6; 435/7.1; 435/252.3; 435/254.2; 435/320.1; 435/325; 435/348; 435/349; 435/358; 435/363; 435/365; 435/367; 435/419; 435/455; 530/350; 536/23.5

(58) Field of Classification Search ................ None
See application file for complete search history.

(56) References Cited

U.S. PATENT DOCUMENTS 5,599,673 A  2/1997  Keating et al.

FOREIGN PATENT DOCUMENTS

WO  WO 96/28537  9/1996

OTHER PUBLICATIONS

Herfst et al. 2004. Journal of Molecular and Cellular Cardiology. 36: 185-193.*
Wang et al. (Nuc. Acids Res. 27: 4609-4618, 1999).*
Kaufman et al (Blood 94: 3178-3184, 1999).*
Phillips, A., J Pharm Pharmacology 53: 1169-1174, 2001.*
Nelson, 1998. Critical Reviews in Clinical Laboratory Sciences. 35(5): 369-414.*
Sambrook et al. 1989, Molecular Cloning: A Laboratory Manual, 2nd edition. Cold Spring Harbor Laboratory Press. p. 11.47.*
Gellens, M.E., et al. (1992). "Primary structure and functional expression of the human cardiac tetrodotoxin-insensitive voltage-dependent sodium channel," *Proc. Nat. Acad. Sci. USA* 89:554-558.
Wang, Qing, et al. (1995). "*SCN5A* Mutations Associated with an Inherited Cardiac Arrhythmia, Long QT Syndrome," *Cell* 80:805-811.
Chen, Qiuyun, et al. (1998). "Genetic basis and molecular mechanism for idiopathic ventricular fibrillation," *Nature* 392:293-296.
Dumaine, Robert, et al. (1999). "Ionic Mechanisms Responsible for the Electrocardiographic Phenotype of the Brugada Syndrome Are Temperature Dependent," *Circ. Res.* 85:803-809.
Rook, Martin B., et al. (1999). "Human *SCN5A* gene mutations alter cardiac sodium channel kinetics and are associated with the Brugada syndrome," *Cardiovas. Res.* 44:507-517.
Deschenes, Isabelle, et al. (2000). "Electrophysical characterization of *SCN5A* mutations causing long QT (E1784K) and Brugada (R1512W and R1432g) syndromes," *Cardiovas. Res.* 46:55-65.
Splawski, Igor, et al. (2002). "Variant of SCN5A Sodium Channel Implicated in Risk of Cardiac Arrhythmia," *Science* 297:1333-1336.

* cited by examiner

*Primary Examiner*—Elizabeth Kemmerer
*Assistant Examiner*—Zachary C. Howard
(74) *Attorney, Agent, or Firm*—Rothwell, Figg, Ernst & Manbeck, P.C.

(57) ABSTRACT

The present invention is directed to a specific mutation in SCN5A which causes drug-induced torsade de pointes or ventricular fibrillation. Persons with the mutation are predisposed to developing drug-induced torsade de pointes or ventricular fibrillation when administered certain drugs. This predisposition can be diagnosed in accordance with the present invention by analyzing the DNA sequence of the SCN5A of an individual. By screening patients for the mutation, drug-induced torsade de pointes or ventricular fibrillation can be avoided. Furthermore, drugs can be tested to determine whether they will cause torsade de pointes or ventricular fibrillation.

7 Claims, No Drawings

COMMON POLYMORPHISM IN SCN5A IMPLICATED IN DRUG-INDUCED CARDIAC ARRHYTHMIA

CROSS-REFERENCE TO RELATED APPLICATIONS

The present application is a national stage filing under 35 U.S.C. §371 of international patent application number PCT/US01/22639 filed 19 Jul. 2001. The present application is further related to and claims priority under 35 U.S.C. §119(e) to U.S. provisional patent application Ser. No. 60/219,738 filed 20 Jul. 2000, incorporated herein by reference.

BACKGROUND OF THE INVENTION

Sudden deaths from cardiac arrhythmias account for 11% of all natural deaths. Arrhythmias frequently result from treatment with medications, most commonly antiarrhythmic drugs.

Long QT Syndrome (LQTS) is a cardiovascular disorder characterized by prolongation of the QT interval on electrocardiogram and presence of syncope, seizures and sudden death. Five genes have been implicated in Romano-Ward syndrome, the autosomal dominant form of LQTS. These genes are KVLQT1, HERG, SCN5A, KCNE1 and KCNE2. Mutations in KVLQT1 and KCNE1 also cause the Jervell and Lange-Nielsen syndrome, a form of LQTS associated with deafness, a phenotypic abnormality inherited in an autosomal recessive fashion.

The present invention relates to an alteration in the SCN5A gene and methods for detecting the alteration.

The publications and other materials used herein to illuminate the background of the invention or provide additional details respecting the practice, are incorporated by reference, and for convenience are respectively grouped in the appended List of References.

The present invention is directed to an alteration in the SCN5A gene and its gene products which are associated with drug-induced torsade de pointes and ventricular fibrillation and to a process for the diagnosis and prevention of these disorders. These drug-induced physical disorders are diagnosed in accordance with the present invention by analyzing the DNA sequence of the SCN5A gene of an individual to be tested and comparing the DNA sequence to the known DNA sequence of the normal gene. Prediction of drug-induced torsade de pointes or ventricular fibrillation will enable practitioners to prevent this disorder using existing medical therapy.

Cardiac arrhythmias are a common cause of morbidity and mortality, accounting for approximately 11% of all natural deaths (Kannel, 1987; Willich et al., 1987). In general, presymptomatic diagnosis and treatment of individuals with life-threatening ventricular tachyarrhythmias is poor, and in some cases medical management actually increases the risk of arrhythmia and death (Cardiac Arrhythmia Suppression Trial II Investigators, 1992). These factors make early detection of individuals at risk for cardiac arrhythmias and arrhythmia prevention high priorities.

Both genetic and acquired factors contribute to the risk of developing cardiac arrhythmias. Long QT syndrome (LQT) is an inherited cardiac arrhythmia that causes abrupt loss of consciousness, syncope, seizures and sudden death from ventricular tachyarrhythmias, specifically torsade depointes and ventricular fibrillation (Ward, 1964; Romano, 1965; Schwartz et al., 1975; Moss et al., 1991). This disorder usually occurs in young, otherwise healthy individuals (Ward, 1964; Romano, 1965; Schwartz et al., 1975). Most LQT gene carriers manifest prolongation of the QT interval on electrocardiograms, a sign of abnormal cardiac repolarization (Vincent et al., 1992). The clinical features of LQT result from episodic cardiac arrhythmias, specifically repolarization-related ventricular tachyarrhythmias like torsade de pointes, named for the characteristic undulating nature of the electrocardiogram in this arrhythmia and ventricular fibrillation (Schwartz et al., 1975; Moss and McDonald, 1971). Torsade de pointes may degenerate into ventricular fibrillation, a particularly lethal arrhythmia. Although LQT is not a common diagnosis, ventricular arrhythmias are very common; more than 300,000 United States citizens die suddenly every year (Kannel, et al., 1987; Willich et al., 1987) and, in many cases, the underlying mechanism may be aberrant cardiac repolarization. LQT, therefore, provides a unique opportunity to study life-threatening cardiac arrhythmias at the molecular level.

Both inherited and acquired forms of LQT have been defined. Acquired LQT and secondary arrhythmias can result from cardiac ischemia, bradycardia and metabolic abnormalities such as low serum potassium or calcium concentration (Zipes, 1987). LQT can also result from treatment with certain medications, including antibiotics, antihistamines, general anesthetics, and, most commonly, antiarrhythmic medications (Zipes, 1987). Inherited forms of LQT can result from mutations in at least five different genes. In previous studies, LQT loci were mapped to chromosome 11p15.5 (KVLQT1 or LQT1) (Keating et al., 1991a; Keating et al., 1991b), 7q35–36 (HERG or LQT2), 3p21–24 (SCN5A or LQT3) (Jiang et al., 1994). Of these, the most common cause of inherited LQT is KVLQT1. Our data indicate that mutations in this gene are responsible for more than 50% of inherited LQT. A fourth LQT locus (LQT4) was mapped to 4q25–27 (Schott et al., 1995). Also, KCNE1 (LQT5) has been associated with long QT syndrome (Splawski et al., 1997b; Duggal et al., 1998). These genes encode ion channels involved in generation of the cardiac action potential. Mutations can lead to channel dysfunction and delayed myocellular repolarization. Because of regional heterogeneity of channel expression with the myocardium, the aberrant cardiac repolarization creates a substrate for arrhythmia. KVLQT1 and KCNE1 are also expressed in the inner ear (Neyroud et al., 1997; Vetter et al., 1996). We and others demonstrated that homozygous or compound heterozygous mutations in each of these genes can cause deafness and the severe cardiac phenotype of the Jervell and Lange-Nielsen syndrome (Neyroud et al., 1997; Splawski et al., 1997a; Schultze-Bahr et al., 1997; Tyson et al., 1997). Loss of functional channels in the ear apparently disrupts the production of endolymph, leading to deafness.

Presymptomatic diagnosis of LQT is currently based on prolongation of the QT interval on electrocardiograms. QTc (QT interval corrected for heart rate; Bazzett, 1920) greater than 0.44 second has traditionally classified an individual as affected. Most LQT patients, however, are young, otherwise healthy individuals, who do not have electrocardiograms. Moreover, genetic studies have shown that QTc is neither sensitive nor specific (Vincent et al., 1992). The spectrum of QTc intervals for gene carriers and non-carriers overlaps, leading to misclassifications. Non-carriers can have prolonged QTc intervals and be diagnosed as affected. Conversely, some LQT gene carriers have QTc intervals of $\leq 0.44$ second but are still at increased risk for arrhythmia. Correct presymptomatic diagnosis is important for effective, gene-specific treatment of LQT.

Autosomal dominant and autosomal recessive forms of this disorder have been reported. Autosomal recessive LQT (also known as Jervell and Lange-Nielsen syndrome) has been associated with congenital neural deafness; this form of LQT is rare (Jervell and Lange-Nielsen, 1957). Autosomal dominant LQT (Romano-Ward syndrome) is more common, and is not associated with other phenotypic abnormalities (Romano et al., 1963; Ward, 1964). A disorder very similar to inherited LQT can also be acquired, usually as a result of pharmacologic therapy (Schwartz et al., 1975; Zipes, 1987).

The data have implications for the mechanism of arrhythmias in LQT. Two hypotheses for LQT have previously been proposed (Schwartz et al., 1994). One suggests that a predominance of left autonomic innervation causes abnormal cardiac repolarization and arrhythmias. This hypothesis is supported by the finding that arrhythmias can be induced in dogs by removal of the right stellate ganglion. In addition, anecdotal evidence suggests that some LQT patients are effectively treated by β-adrenergic blocking agents and by left stellate ganglionectomy (Schwartz et al., 1994). The second hypothesis for LQT-related arrhythmias suggests that mutations in cardiac-specific ion channel genes, or genes that modulate cardiac ion channels, cause delayed myocellular repolarization. Delayed myocellular repolarization could promote reactivation of L-type calcium channels, resulting in secondary depolarizations (January and Riddle, 1989). These secondary depolarizations are the likely cellular mechanism of torsade de pointes arrhythmias (Surawicz, 1989). This hypothesis is supported by the observation that pharmacologic block of potassium channels can induce QT prolongation and repolarization-related arrhythmias in humans and animal models (Antzelevitch and Sicouri, 1994). The discovery that one form of LQT results from mutations in a cardiac potassium channel gene supports the myocellular hypothesis.

In theory, mutations in a cardiac sodium channel gene could cause LQT. Voltage-gated sodium channels mediate rapid depolarization in ventricular myocytes, and also conduct a small current during the plateau phase of the action potential (Attwell et al., 1979). Subtle abnormalities of sodium channel function (e.g., delayed sodium channel inactivation or altered voltage-dependence of channel inactivation) could delay cardiac repolarization, leading to QT prolongation and arrhythmias. In 1992, Gellens and colleagues cloned and characterized a cardiac sodium channel gene, SCN5A (Gellens et al., 1992). The structure of this gene was similar to other, previously characterized sodium channels, encoding a large protein of 2016 amino acids. These channel proteins contain four homologous domains (DI-DIV), each of which contains six putative membrane spanning segments (S1–S6). SCN5A was mapped to chromosome 3p21, making it an excellent candidate gene for LQT3 (George et al., 1995), and this gene was then proved to be associated with LQT3 (Wang et al., 1995).

In 1994, Warmke and Ganetzky identified a novel human cDNA, human ether a-go-go related gene (HERG, Warmke and Ganetzky, 1994). HERG was localized to human chromosome 7 by PCR analysis of a somatic cell hybrid panel (Warmke and Ganetzky, 1994) making it a candidate for LQT2. It has predicted amino acid sequence homology to potassium channels. HERG was isolated from a hippocampal cDNA library by homology to the *Drosophila* ether a-go-go gene (eag), which encodes a calcium-modulated potassium channel (Bruggemann et al., 1993). HERG is not the human homolog of eag, however, sharing only ~50% amino acid sequence homology. HERG has been shown to be associated with LQT2 (Curran et al., 1995).

LQT1 was found to be linked with the gene KVLQT1 (Q. Wang et al., 1996). Sixteen families with mutations in KVLQT1 were identified and characterized and it was shown that in all sixteen families there was complete linkage between LQT1 and KVLQT1. KVLQT1 was mapped to chromosome 11p15.5 making it a candidate gene for LQT1. KVLQT1 encodes a protein with structural characteristics of potassium channels, and expression of the gene as measured by Northern blot analysis demonstrated that KVLQT1 is most strongly expressed in the heart. One intragenic deletion and ten different missense mutations which cause LQT were identified in KVLQT1. These data define KVLQT1 as a novel cardiac potassium channel gene and show that mutations in this gene cause susceptibility to ventricular tachyarrhythmias and sudden death.

It was known that one component of the $I_{Ks}$ channel is minK, a 130 amino acid protein with a single putative transmembrane domain (Takumi et al., 1988; Goldstein and Miller, 1991; Hausdorff et al., 1991; Takumi et al., 1991; Busch et al., 1992; Wang and Goldstein, 1995; KW Wang et al., 1996). The size and structure of this protein made it unlikely that minK alone forms functional channels (Attali et al., 1993; Lesage et al., 1993). Evidence was presented that KVLQT1 and minK coassemble to form the cardiac $I_{Ks}$ potassium channel (Sanguinetti et al., 1996). $I_{Ks}$ dysfunction is a cause of cardiac arrhythmia. It was later shown that mutations in KCNE1 (which encodes minK) also can result in LQT (Splawski et al., 1997b).

SUMMARY OF THE INVENTION

The present invention is directed to one mutation in SCN5A which has been associated with drug-induced torsade de pointes and ventricular fibrillation.

In one aspect of the present invention, the association of a specific mutation in SCN5A with torsade de pointes and ventricular fibrillation is provided.

In a second aspect of the present invention, analysis of the SCN5A gene is provided for an early diagnosis of subjects susceptible to drug-induced torsade de pointes and ventricular fibrillation. The diagnostic method comprises analyzing the DNA sequence of SCN5A of an individual to be tested and comparing it with the DNA sequence of the native, non-variant gene. The ability to predict predisposition to drug-induced torsade de pointes and ventricular fibrillation will enable physicians to prevent these conditions in the susceptible patients by appropriate prescribing of medication.

The invention is further directed to methods of screening drug candidates which can be used to treat or prevent torsade de pointes or ventricular fibrillation in patients with an SCN5A mutation which predisposes persons to drug-induced torsade de pointes and ventricular fibrillation. Another aspect of the invention is a method of screening drugs to determine whether they may result in the development of torsade de pointes or ventricular fibrillation when administered to a person with a mutation in SCN5A.

DETAILED DESCRIPTION OF THE INVENTION

The present invention is directed to determining whether a patient has a specific mutation in SCN5A which will predispose him to drug-induced torsade depointes and ventricular fibrillation. The present invention is further directed to methods of screening humans for the presence of this SCN5A gene variant which causes drug-induced torsade de pointes and ventricular fibrillation. Since this predisposition can now be detected earlier (i.e., before symptoms appear) and more definitively, better treatment options will be available for those individuals identified as having the mutation. The present invention is also directed to methods for screening for drugs useful in treating or preventing torsade de pointes and ventricular fibrillation.

The present invention provides methods of screening the SCN5A gene to identify the specific mutation. Such methods may further comprise the step of amplifying a portion of the SCN5A gene, and may further include a step of providing a set of polynucleotides which are primers for amplification of said portion of the SCN5A gene. The method is useful for identifying mutations for use in either diagnosis of or prognosis of predisposition to drug-induced torsade de pointes and ventricular fibrillation.

The present invention is further directed to a method for screening drug candidates to identify drugs useful for treating or preventing torsade depointes and ventricular fibrillation. Drug screening is performed by expressing mutant SCN5A in cells, such as oocytes, mammalian cells or transgenic animals, and assaying the effect of a drug candidate on the SCN5A sodium channel. The effect is compared to the wild-type SCN5A sodium channel activity.

The invention is further directed to methods of screening drugs to determine whether administration of a specific drug to a person with the mutant SCN5A will result in torsade de pointes or ventricular fibrillation in the person.

Finally, the invention is directed to methods of testing compounds to determine if they are capable of modulating the activity of a mutated SCN5A protein.

Alterations in the SCN5A gene can result in a change in many physical characteristics of the $Na^+$ channel. These include, but are not limited to, ion specificity, length of inactivation, amplitude of current, voltage dependence of activation or inactivation, kinetics, and voltage threshold for activation. The prior art teaches a variety of physical properties whose activities are changed as a result of the presence of altered SCN5A. Publications which discuss some of these changes include Veldkamp et al. (2000), Kambouris et al. (2000), Deschenes et al. (2000), Rook et al. (1999), Antzelevitch et al. (1999), Couderc et al. (1999) and Wang et al. (1996). These altered physical characteristics can be modulated, i.e., they can be either increased or decreased by a measurable amount, by treatment with certain drugs. It is a desire to screen for drugs which will modulate the mutated SCN5A channels. In most cases it would be desirable to modulate the mutated SCN5A channels so that they will behave more like wild-type SCN5A channels and will result in beneficial effects for persons whose genome contains mutated SCN5A and who are being treated with these drugs. In the case of mutated SCN5A channels that have no detectable difference in activity when compared to wild-type SCN5A channels in the absence of certain drugs but exhibit altered functional characteristics compared to wild-type SCN5A channels in the presence of certain drugs, it would be desirable to use the mutated SCN5A channels to find drugs that would not modulate the activity of the mutated SCN5A channel when compared to the wild-type SCN5A channel.

According to the diagnostic and prognostic method of the present invention, alteration of the wild-type SCN5A gene is detected. In addition, the method can be performed by detecting the wild-type SCN5A gene and confirming the lack of a predisposition to drug-induced torsade de pointes and ventricular fibrillation as a result of this locus.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology.

The presence of the SCN5A mutation which predisposes one to drug-induced torsade de pointes and ventricular fibrillation may be ascertained by testing any tissue of a human for the mutation of the SCN5A gene. For example, a person who has inherited the SCN5A mutation in the germline would be predisposed to drug-induced torsade depointes and ventricular fibrillation. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for the mutation of the SCN5A gene. Alteration of a wild-type SCN5A allele can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997). Other techniques for detecting mutations are known in the art and can be used. For example, single base extension methods, which are described in e.g., U.S. Pat. Nos. 5,846,710, 6,004,744, 5,888,819 and 5,856,092, can be used to determine the identity of a single base to determine whether that location is mutated.

Detection of point mutations may be accomplished by molecular cloning of the SCN5A alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); and 6) allele-specific PCR (Ruano and Kidd, 1989). For allele-specific PCR, primers are used which hybridize at their 3' ends to the particular SCN5A mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type SCN5A gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the MRNA or gene but can be a segment of either.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the SCN5A gene can also be detected using Southern hybridization.

DNA sequences of the SCN5A gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified SCN5A sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Editorial, Nature Genetics, 1996). Also see Fodor (1997).

The most definitive test for mutations in a candidate locus is to directly compare genomic SCN5A sequences from patients with those from a control population. Alternatively, one could sequence messenger RNA after amplification, e.g., by PCR, thereby eliminating the necessity of determining the exon structure of the candidate gene.

Alteration of wild-type genes can also be detected by screening for alteration of wild-type SCN5A protein. For example, monoclonal antibodies immunoreactive with SCN5A can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered SCN5A protein can be used to detect alteration of the wild-type SCN5A gene. Functional assays, such as protein binding determinations, can be used. In addition, assays can be used which detect SCN5A biochemical function.

A mutant SCN5A gene or gene product can also be detected in other human body samples, such as serum, stool, urine and sputum. The same techniques discussed above for detection of mutant genes or gene products in tissues can be applied to other body samples. By screening such body samples, a simple early diagnosis can be achieved for predisposition to drug-induced torsade de pointes and ventricular fibrillation.

The primer pairs of the present invention are useful for determination of the nucleotide sequence of a particular SCN5A allele using PCR. The pairs of single-stranded DNA primers for SCN5A can be annealed to sequences within or surrounding the SCN5A gene in order to prime amplifying DNA synthesis of the gene itself. Allele-specific primers can also be used. Such primers anneal only to the particular SCN5A mutant allele, and thus will only amplify a product in the presence of the mutant allele as a template.

It is known that individuals with the wild-type SCN5A gene are not predisposed to drug-induced torsade de pointes and ventricular fibrillation. However, it is here shown that a specific mutation which interferes with the function of the SCN5A gene product is involved in predisposition to drug-induced torsade depointes and ventricular fibrillation. Thus, the presence of an altered (or a mutant) SCN5A gene which produces a protein having a loss of function, or altered function, directly causes predisposition to torsade de pointes and ventricular fibrillation. In order to detect an SCN5A gene mutation, a biological sample is prepared and analyzed for a difference between the sequence of the allele being analyzed and the sequence of the wild-type allele. Mutant SCN5A alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations are then used for the diagnostic and prognostic methods of the present invention.

Definitions

The present invention employs the following definitions.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the SCN5A region are preferably complementary to, and hybridize specifically to sequences in the SCN5A region or in regions that flank a target region therein. SCN5A sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the SCN5A polypeptide and fragments thereof or to polynucleotide sequences from the SCN5A region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the SCN5A polypeptide or fragment. Monoclonal antibodies may be made by injecting mice with the protein polypeptides, fusion proteins or fragments thereof. Monoclonal antibodies will be screened by ELISA and tested for specific immunoreactivity with SCN5A polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $M^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"SCN5A Allele" refers, respectively, to normal alleles of the SCN5A locus as well as alleles of SCN5A carrying variations that cause predisposition to drug-induced torsade de pointes and ventricular fibrillation.

"SCN5A Locus", "SCN5A Gene", "SCN5A Nucleic Acids" or "SCN5A Polynucleotide" each refer to polynucleotides, all of which are in the SCN5A region, respectively, that are likely to be expressed in normal tissue, certain alleles of which result in drug-induced predisposition to torsade de pointes and ventricular fibrillation. The SCN5A locus is intended to include coding sequences, intervening sequences and regulatory elements controlling transcription and/or translation. The SCN5A locus is intended to include all allelic variations of the DNA sequence.

These terms, when applied to a nucleic acid, refer to a nucleic acid which encodes a human SCN5A polypeptide, fragment, homolog or variant, including, e.g., protein fusions or deletions. The nucleic acids of the present invention will possess a sequence which is either derived from, or substantially similar to a natural SCN5A-encoding gene or one having substantial homology with a natural SCN5A-encoding gene or a portion thereof.

The SCN5A gene or nucleic acid includes normal alleles of the SCN5A gene including silent alleles having no effect on the amino acid sequence of the SCN5A polypeptide as well as alleles leading to amino acid sequence variants of the SCN5A polypeptide that do not substantially affect its function. These terms also include alleles having one or more mutations which adversely affect the function of the SCN5A polypeptide. A mutation may be a change in the SCN5A nucleic acid sequence which produces a deleterious change in the amino acid sequence of the SCN5A polypeptide, resulting in partial or complete loss of SCN5A function or may be a change in the nucleic acid sequence which results in the loss of effective SCN5A expression or the production of aberrant forms of the SCN5A polypeptide.

The SCN5A nucleic acid may be that of SEQ ID NO:1 (wild-type) or it may be an allele as that of SEQ ID NO:3 (mutant) which includes the specific mutation which predisposes one to drug-induced torsade de pointes and ventricular fibrillation.

Nucleic acid according to the present invention may include a sequence different from the sequences shown as SEQ ID NOs:1 and 3 yet encode a polypeptide with the same amino acid sequence as shown as SEQ ID NOs:2 and 4. That is, nucleic acids of the present invention include sequences which are degenerate as a result of the genetic code.

The SCN5A gene also refers to (a) any DNA sequence that (i) hybridizes to the complement of the DNA sequences that encode the amino acid sequence set forth by SEQ ID NOs:1 and 3 under highly stringent conditions (Ausubel et al., 1992) and (ii) encodes a gene product functionally equivalent to that of SEQ ID NO:2 or SEQ ID NO:4, or (b) any DNA sequence that (i) hybridizes to the complement of the DNA sequences that encode one of the amino acid sequences set forth by SEQ ID NOs:2 and 4 under less stringent conditions, such as moderately stringent conditions (Ausubel et al., 1992) and (ii) encodes a gene product functionally equivalent to SCN5A as shown by SEQ ID NO:2 or 4. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the SCN5A region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with an SCN5A-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the SCN5A locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NO:1 or 3, its complement or functionally equivalent nucleic acid sequences. The present invention does not include nucleic acids which exist in the prior art. That is, the present invention includes all nucleic acids having at least 8 nucleotides derived from SEQ ID NO:1 or 3 with the proviso that it does not include nucleic acids existing in the prior art.

"SCN5A protein" or "SCN5A polypeptide" refers to a protein or polypeptide encoded by the SCN5A locus, variants or fragments thereof. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native SCN5A sequence, preferably in excess of about 90%, and more preferably at least about 95% homologous. Also included are proteins encoded by DNA which hybridize under high or low stringency conditions, to SCN5A-encoding nucleic acids and closely related polypeptides or proteins retrieved by antisera to the SCN5A protein.

The SCN5A polypeptide may be that shown by SEQ ID NO:2 or 4 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the SCN5A polypeptide. Such polypeptides may have an amino acid sequence which differs from that set forth in SEQ ID NO:2 or 4 by one or more of addition, substitution, deletion or insertion of one or more amino acids. Preferred such polypeptides have SCN5A function.

Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the SCN5A polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the SCN5A polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural SCN5A polypeptide.

"Probes". Polynucleotide polymorphisms associated with SCN5A alleles which predispose to torsade de pointes and ventricular fibrillation are detected by hybridization with a polynucleotide probe which forms a stable hybrid with that of the target sequence, under stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that it is meant to be read as "high stringency" conditions are used.) Since such indications identify neutral DNA polymorphisms as well as mutations, these indications need further analysis to demonstrate detection of an SCN5A susceptibility allele.

Probes for SCN5A alleles may be derived from the sequences of the SCN5A region, its cDNA, functionally equivalent sequences, or the complements thereof. The probes may be of any suitable length, which span all or a portion of the SCN5A region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding SCN5A are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether MRNA encoding SCN5A is present in a cell or tissue. The present invention does not include probes which exist in the prior art. That is, the present invention includes all probes having at least 8 nucleotides derived from SEQ ID NO:1 or 3, with the proviso that they do not include probes existing in the prior art.

Similar considerations and nucleotide lengths are also applicable to primers which may be used for the amplification of all or part of the SCN5A gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether MRNA encoding SCN5A is present in a cell or tissue. The present invention includes all novel primers having at least 8 nucleotides derived from the SCN5A locus for amplifying the SCN5A gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for SCN5A polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of SCN5A polypeptides. Immunological activities include both immunogenic function in a target immune system, as well as sharing of immunological epitopes for binding, serving as either a competitor or substitute antigen for an epitope of the SCN5A protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for SCN5A polypeptides or fragments thereof is described below.

The present invention also provides for fusion polypeptides, comprising SCN5A polypeptides and fragments. Homologous polypeptides may be fusions between two or more SCN5A polypeptide sequences or between the sequences of SCN5A and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the SCN5A polypeptides from other biological material, such as from cells transformed with recombinant nucleic acids encoding SCN5A, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

An SCN5A protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/bl2.html) (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used. The averaging is to be performed as in this example of SEQ ID NOs:5 and 6.

5'-ACCGTAGCTACGTACGTATATAGAAAGGGCGCGATCGTCGTCGCGTATGACGAC   (SEQ ID NO:5)

TTAGCATGC-3'

5'-ACCGGTAGCTACGTACGTTATTTAGAAAGGGGTGTGTGTGTGTGTAAACCGGG   (SEQ ID NO:6)

GTTTTCGGGATCGTCCGTCGCGTATGACGACTTAGCCATGCACGGTATATCGTATTA

GGACTAGCGATTGACTAG-3'

The program "BLAST 2 Sequences" shows differing alignments of these two nucleic acids depending upon the parameters which are selected. As examples, four sets of parameters were selected for comparing SEQ ID NOs:5 and 6 (gap x_dropoff was 50 for all cases), with the results shown in Table 1. It is to be noted that none of the sets of parameters selected as shown in Table 1 is necessarily the best set of parameters for comparing these sequences. The percent homology is calculated by multiplying for each region showing identity the fraction of bases of the shorter strand within a region times the percent identity for that region and adding all of these together. For example, using the first set of parameters shown in Table 1, SEQ ID NO:5 is the short sequence (63 bases), and two regions of identity are shown, the first encompassing bases 4–29 (26 bases) of SEQ ID NO:5 with 92% identity to SEQ ID NO:6 and the second encompassing bases 39–59 (21 bases) of SEQ ID NO:5 with 100% identity to SEQ ID NO:6. Bases 1–3, 30–38 and 60–63 (16 bases) are not shown as having any identity with SEQ ID NO:6. Percent homology is calculated as: (26/63)(92)+(21/63)(100)+(16/63)(0)=71.3% homology. The percents of homology calculate using each of the four sets of parameters shown are listed in Table 1. Several other combinations of parameters are possible, but they are not listed for the sake of brevity. It is seen that each set of parameters resulted in a different calculated percent homology. Because the result yielding the highest percent homology is to be used, based solely on these four sets of parameters one would state that SEQ ID NOs:5 and 6 have 87.1% homology. Again it is to be noted that use of other parameters may show an even higher homology for SEQ ID NOs:5 and 6, but for brevity not all the possible results are shown.

TABLE 1

| Match | Mis-match | Open Gap | Extension Gap | Regions of identity (%) | | Homology |
|---|---|---|---|---|---|---|
| 1 | −2 | 5 | 1 | 4–29 of 5 and 5–31 of 6 (92%) | 39–59 of 5 and 71–91 of 6 (100%) | 71.3 |
| 1 | −2 | 2 | 1 | 4–29 of 5 and 5–31 of 6 (92%) | 33–63 of 5 and 64–96 of 6 (93%) | 83.7 |
| 1 | −1 | 5 | 1 | — | 30–59 of 5 and 61–91 of 6 (93%) | 44.3 |
| 1 | −1 | 2 | 1 | 4–29 of 5 and | 30–63 of 5 and 61–96 of 6 | 87.1 |

TABLE 1-continued

| Match | Mis-match | Open Gap | Extension Gap | Regions of identity (%) | | Homology |
|---|---|---|---|---|---|---|
| | | | | 5–31 of 6 (92%) | (91%) | |

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type SCN5A nucleic acid or wild-type SCN5A polypeptide. The modified polypeptide will be substantially homologous to the wild-type SCN5A polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type SCN5A polypeptide. Alternatively, the similarity of function (activity) of the modified polypeptide may be higher than the activity of the wild-type SCN5A polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type SCN5A gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

1. Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers (1981) or the triester method according to Matteucci and Caruthers (1981) and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the SCN5A gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, Cold Spring Harbor, N.Y. (1983). See also, e.g., U.S. Pat. Nos. 5,691,198; 5,735,500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the SCN5A nucleic acid or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.) (1979). Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of SCN5A polypeptides.

The probes and primers based on the SCN5A gene sequences disclosed herein are used to identify homologous SCN5A gene sequences and proteins in other species. These gene sequences and proteins are used in the diagnostic/prognostic, therapeutic and drug screening methods described herein for the species from which they have been isolated.

2. Methods of Use: Drug Screening

The invention is particularly useful for screening compounds by using SCN5A proteins in transformed cells, transfected oocytes or transgenic animals. Since mutations in the SCN5A protein can alter the functioning of the cardiac sodium channel, candidate drugs are screened for effects on the channel using cells containing either a normal SCN5A protein or a mutant SCN5A protein. The drug is added to the cells in culture or administered to a transgenic animal and the effect on the induced current of the wild-type sodium channel is compared to the induced current of a cell or animal containing the mutant sodium channel. Drug candidates which alter the induced current to a more normal level are useful for treating or preventing drug-induced torsade de pointes and ventricular fibrillation. The same type of experiments are performed to screen drugs, not for their ability to treat or prevent drug-induced torsade depointes and ventricular fibrillation, but rather to determine whether a drug is one which may induce torsade de pointes and ventricular fibrillation. If addition of a drug to cells or an animal expressing a mutant SCN5A results in an induced $Na^+$ current different from that in the absence of the drug, the drug is one which may induce torsade de pointes and ventricular fibrillation in persons with the mutation. Similar studies may be performed on cells or animals expressing wild-type SCN5A to determine whether the test drug has a similar effect on the induced $Na^+$ current in wild-type cells or animals. If a similar effect is seen then persons with the mutant SCN5A are at no greater risk than are persons with wild-type SCN5A, but if the induced current in drug-treated mutant cells or animals differs by a greater amount than that in drug-treated wild-type cells or animals from the non-drug-treated cells or animals, then persons with the mutation are at greater risk of having the drug induce torsade de pointes and ventricular fibrillation.

This invention is particularly useful for screening compounds by using the SCN5A polypeptide or binding fragment thereof in any of a variety of drug screening techniques.

The SCN5A polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an SCN5A polypeptide or fragment and the agent being tested, or examine the degree to which the formation of a complex between an SCN5A polypeptide or fragment and a known ligand is interfered with by the agent being tested.

Thus, the present invention provides methods of screening for drugs comprising contacting such an agent with an SCN5A polypeptide or fragment thereof and assaying (i) for the presence of a complex between the agent and the SCN5A polypeptide or fragment, or (ii) for the presence of a complex between the SCN5A polypeptide or fragment and a ligand, by methods well known in the art. In such competitive binding assays the SCN5A polypeptide or fragment is typically labeled. Free SCN5A polypeptide or fragment is separated from that present in a protein:protein complex, and the amount of free (i.e., uncomplexed) label is a measure of the binding of the agent being tested to SCN5A or its interference with SCN5A:ligand binding, respectively. One may also measure the amount of bound, rather than free, SCN5A. It is also possible to label the ligand rather than the SCN5A and to measure the amount of ligand binding to SCN5A in the presence and in the absence of the drug being tested.

Another technique for drug screening provides high throughput screening for compounds having suitable binding affinity to the SCN5A polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with SCN5A polypeptide and washed. Bound SCN5A polypeptide is then detected by methods well known in the art.

Purified SCN5A can be coated directly onto plates for use in the aforementioned drug screening techniques. However, non-neutralizing antibodies to the polypeptide can be used to capture antibodies to immobilize the SCN5A polypeptide on the solid phase.

This invention also contemplates the use of competitive drug screening assays in which neutralizing antibodies capable of specifically binding the SCN5A polypeptide compete with a test compound for binding to the SCN5A polypeptide or fragments thereof. In this manner, the antibodies can be used to detect the presence of any peptide which shares one or more antigenic determinants of the SCN5A polypeptide.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to, or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an SCN5A specific binding partner, or to find mimetics of the SCN5A polypeptide.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of drug-induced torsade de pointes or ventricular fibrillation, use of such a substance in the manufacture of a composition for administration, e.g., for treatment of drug-induced torsade de pointes and ventricular fibrillation, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

3. Methods of Use: Nucleic Acid Diagnosis and Diagnostic Kits

In order to detect the presence of an SCN5A allele predisposing an individual to drug-induced torsade de pointes and ventricular fibrillation, a biological sample such as blood is prepared and analyzed for the presence or absence of susceptibility alleles of SCN5A. In order to detect the presence of predisposition to drug-induced torsade de pointes and ventricular fibrillation or as a prognostic indicator, a biological sample is prepared and analyzed for the presence or absence of mutant alleles of SCN5A. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant SCN5A sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of SCN5A. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al. (1986).

Two-step label amplification methodologies are known in the art. These assays work on the principle that a small ligand (such as digoxigenin, biotin, or the like) is attached to a nucleic acid probe capable of specifically binding SCN5A. Allele specific probes are also contemplated within the scope of this example and exemplary allele specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting SCN5A. Thus, in one example to detect the presence of SCN5A in a cell sample, more than one probe complementary to the gene is employed and in particular, the number of different probes is alternatively two, three, or five different nucleic acid probe sequences. In another example, to detect the presence of mutations in the SCN5A gene sequence in a patient, more than one probe complementary to these genes is employed where the cocktail includes probes capable of binding to the allele-specific mutations identified in populations of patients with alterations in SCN5A. In this embodiment, any number of probes can be used, and will preferably include probes corresponding to the gene mutation identified as predisposing an individual to drug-induced torsade de pointes and ventricular fibrillation.

4. Methods of Use: Peptide Diagnosis and Diagnostic Kits

The presence of predisposition to drug-induced torsade de pointes and ventricular fibrillation can also be detected on the basis of the alteration of wild-type SCN5A polypeptide. Such alterations can be determined by sequence analysis in accordance with conventional techniques. More preferably, antibodies (polyclonal or monoclonal) are used to detect differences in, or the absence of SCN5A peptides. Techniques for raising and purifying antibodies are well known in the art, and any such techniques may be chosen to achieve the preparations claimed in this invention. In a preferred embodiment of the invention, antibodies will immunoprecipitate SCN5A proteins from solution as well as react with these proteins on Western or immunoblots of polyacrylamide gels. In another preferred embodiment, antibodies will detect SCN5A proteins in paraffin or frozen tissue sections, using immunocytochemical techniques.

Preferred embodiments relating to methods for detecting SCN5A or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

5. Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., SCN5A polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., SCN5A polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved SCN5A polypeptide activity or stability or which act as inhibitors, agonists, antagonists, etc. of SCN5A polypeptide activity. By virtue of the availability of cloned SCN5A sequences, sufficient amounts of the SCN5A polypeptide may be made available to perform such analytical studies as x-ray crystallography. In addition, the knowledge of the SCN5A protein sequences provided herein will guide those employing computer modeling techniques in place of, or in addition to x-ray crystallography.

6. Methods of Use: Gene Therapy

According to the present invention, a method is also provided of supplying wild-type SCN5A function to a cell which carries a mutant SCN5A allele. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the SCN5A gene or fragment, where applicable, may be employed in gene therapy methods in order to increase the amount of the expression products of such gene in cells. It may also be useful to increase the level of expression of wild-type SCN5A even in those heart cells in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of SCN5A polypeptide in the cells.

A virus or plasmid vector (see further details below), containing a copy of the SCN5A gene linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (1998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes SCN5A, expression will produce SCN5A. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to heart tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry an SCN5A susceptibility allele are treated with a gene delivery vehicle such that some or all of their heart precursor cells receive at least one additional copy of a functional normal SCN5A allele. In this step, the treated individuals have reduced risk of drug-induced torsade de pointes and ventricular fibrillation to the extent that the effect of the susceptible allele has been countered by the presence of the normal allele.

7. Methods of Use: Peptide Therapy

Peptides which have SCN5A activity can be supplied to cells which carry a mutant or missing SCN5A allele. Protein can be produced by expression of the cDNA sequence in bacteria, for example, using known expression vectors. Alternatively, SCN5A polypeptide can be extracted from SCN5A-producing mammalian cells. In addition, the techniques of synthetic chemistry can be employed to synthesize SCN5A protein. Any of such techniques can provide the preparation of the present invention which comprises the SCN5A protein. The preparation is substantially free of other human proteins. This is most readily accomplished by synthesis in a microorganism or in vitro.

Active SCN5A molecules can be introduced into cells by microinjection or by use of liposomes, for example. Alternatively, some active molecules may be taken up by cells, actively or by diffusion. Supply of molecules with SCN5A activity should lead to partial reversal of drug-induced torsade depointes and ventricular fibrillation. Other molecules with SCN5A activity (for example, peptides, drugs or organic compounds) may also be used to effect such a reversal. Modified polypeptides having substantially similar function are also used for peptide therapy.

8. Methods of Use: Transformed Hosts

Animals for testing therapeutic agents can be selected after mutagenesis of whole animals or after treatment of germline cells or zygotes. Such treatments include insertion of mutant SCN5A alleles, usually from a second animal species, as well as insertion of disrupted homologous genes. Alternatively, the endogenous SCN5A gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the predisposition to drug-induced torsade de pointes and ventricular fibrillation must be assessed. If the test substance prevents or suppresses the appearance of drug-induced torsade de pointes and ventricular fibrillation, then the test substance is a candidate therapeutic agent for prevention of drug-induced torsade de pointes and ventricular fibrillation. These animal models provide an extremely important testing vehicle for potential therapeutic products.

The identification of the association between the SCN5A gene mutation and drug-induced torsade de pointes and ventricular fibrillation permits the early presymptomatic screening of individuals to identify those at risk for developing drug-induced torsade de pointes and ventricular fibrillation. To identify such individuals, the SCN5A alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal SCN5A gene or appropriate fragment (coding sequence or genomic sequence) are determined and then compared, or (2) the RNA transcripts of the SCN5A gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the SCN5A gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal SCN5A gene.

Alternatively, polymerase chain reactions (PCRs) are performed with primer pairs for the 5' region or the exons of the SCN5A gene. PCRs can also be performed with primer pairs based on any sequence of the normal SCN5A gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common SCN5A gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal SCN5A gene and defective genes. This comparison is performed in steps using small (~500 bp) restriction fragments of the SCN5A gene as the probe. First, the SCN5A gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the SCN5A gene fragments are transcribed in vitro using the SP6 transcription system, well known in the art, in the presence of $[\alpha\text{-}^{32}P]GTP$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the SCN5A fragment and the SCN5A allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Genetic testing will enable practitioners to identify individuals at risk for drug-induced torsade de pointes and ventricular fibrillation at, or even before, birth. Presymptomatic diagnosis of drug-induced torsade de pointes and ventricular fibrillation will enable prevention of this disorder. Genetic testing and improved mechanistic understanding of drug-induced torsade de pointes and ventricular fibrillation provide the opportunity for prevention of life-threatening arrhythmias through rational therapies. It is possible, for example, that sodium channel blocking agents may be an effective treatment for patients with mutations that alter the function of SCN5A. Finally, these studies may provide insight into mechanisms underlying common arrhythmias, as these arrhythmias are often associated with abnormal cardiac repolarization and may result from a combination of inherited and acquired factors.

9. Pharmaceutical Compositions and Routes of Administration

The SCN5A polypeptides, antibodies, peptides and nucleic acids of the present invention can be formulated in pharmaceutical compositions, which are prepared according to conventional pharmaceutical compounding techniques. See, for example, *Remington's Pharmaceutical Sciences*, 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731A and WO 90/07936.

EXAMPLES

The present invention is further detailed in the following examples, which are offered by way of illustration and are not intended to limit the invention in any manner. Standard techniques well known in the art or the techniques specifically described below are utilized.

Example 1

Identification of an SCN5A Mutation Associated with Drug-induced Torsade de Pointes Arrhythmias frequently result from treatment with medications, cost commonly antiarrhythmic drugs. To determine the genetic basis for these arrhythmias, individuals with drug-induced torsade de pointes and ventricular fibrillation were screened for mutations in known arrhythmia genes. One of the genes which was screened is SCN5A the sequence of which is given by SEQ ID NO:1. The encoded SCN5A protein is shown as SEQ ID NO:2. This sequence is also available from GenBank as Accession No. NM000335. An SCN5A variant, shown as SEQ ID NO:3 was found in four African-American individuals, three of whom experienced arrhythmia after amiodarone treatment and one after infusion of brevital. This variant was also found in two additional African-American individuals. All six individuals had prolongation of their QT interval on electrocardiograms which was exacerbated in the four drug-induced arrhythmia cases.

The mutation which is seen in these individuals is the change at base 3308 of the SCN5A coding sequence wherein the wild-type C is an A in the mutant version. This results in the encoded protein having a tyrosine at amino acid residue 1103 rather than the serine found in the wild-type at this location. This S1103Y variant was present in 11% of the tested African-American individuals, but was not seen in other ethnic groups.

The S1103Y variant was detected on a 0.5X MDE (Mutation Detection Enhancement; FMC BioProducts) gel run overnight at 500V at room temperature.

Example 2

Screening Assay for Drug Candidates Useful for Treating or Preventing Drug-induced Torsade de Pointes or Ventricular Fibrillation Persons with SCN5A encoding a protein of SEQ ID NO:4 are susceptible to drug-induced torsade de pointes and ventricular fibrillation. Drugs may prevent these effects by means, e.g., binding to the mutated SCN5A in a manner which prevents the drug-induced effects. Assays for screening for such drugs, irrelevant of the mechanism of action of such drugs in preventing the drug-induced torsade de pointes and ventricular fibrillation, can be performed.

A. In Vitro Assay

The assay comprises placing a first set of cells expressing the mutant SCN5A into a bathing solution, inducing a current across the SCN5A sodium channel and measuring a first induced current. A second set of cells which expresses wild-type SCN5A is placed into a separate bathing solution, a current is induced and a second induced current is measured. A drug is added to the first set of cells in solution, a current is induced, and a third induced current is measured. The order of measuring the second current relative to measuring the first and third currents is irrelevant. If the drug results in the third induced current being more similar to the second induced current than is the first induced current, then the drug is a drug candidate for treating persons with the mutated SCN5A to treat or prevent the occurrence of drug-induced torsade de pointes or ventricular fibrillation. Preferably the cells being used which express the mutant SCN5A do not also express wild-type SCN5A. Such cells are prepared by making transgenic cells or by injecting cells such as frog oocytes with RNA to express the mutant SCN5A. The term "cells" in this disclosure includes tissue samples as well as single cells.

B. In Vivo Assay

An assay similar to the in vitro method is performed on transgenic animals wherein the animals express either wild-type SCN5A or the mutant SCN5A. Currents are induced and measurements of the induced currents are made. The transgenic animals expressing mutant SCN5A have measurements made without drug treatment and with drug treatment and the measurements are compared to the induced current in animals expressing the wild-type SCN5A. If the induced current in the drug-treated transgenic animal is more similar to the induced current in the wild-type animal than is the induced current in the nondrug-treated mutant animal as compared to the induced current in the wild-type animal, then the drug is a drug candidate for treating persons with the mutated SCN5A.

Example 3

Assays to Determine Whether a Drug can Induce Torsade de Pointes in a Person with an SCN5A Mutation Certain drugs are known to cause torsade depointes and ventricular fibrillation in certain individuals. As demonstrated herein, persons with the SCN5A S 1103Y mutation are predisposed to such drug-induced effects with certain drugs. Assays to determine whether other drugs may also cause torsade de pointes and ventricular fibrillation in persons with this mutation can be performed.

A. In Vitro Assay

One assay comprises placing cells expressing the mutant SCN5A into a bathing solution, inducing a current across the SCN5A $Na^+$ channel and measuring the induced current, then adding the drug to be tested to the bathing solution, inducing a current and measuring this second induced current. If the drug has no effect upon the induced current then it will not induce torsade de pointes and ventricular fibrillation in persons with this mutation as a result of the mutation. If the drug does affect the induced current then it may induce torsade de pointes and ventricular fibrillation in persons with the mutation.

B. In Vivo Assay

An in vivo assay to test whether a drug may cause drug-induced torsade de pointes or ventricular fibrillation in a person with a specific mutation in SCN5A is to prepare a transgenic animal with mutant SCN5A such that the mutant SCN5A is expressed, induce a current across the SCN5A $Na^+$ channel of cells expressing the mutant SCN5A, administer the drug to be tested to the transgenic animal, induce a current and compare this second current with the current induced in the absence of the drug. If the drug has no effect on the induced current it will not cause torsade de pointes or ventricular fibrillation in a person with the SCN5A mutation as a result of the mutation.

C. In Vivo Assay

A second in vivo assay is to prepare a transgenic animal which expresses a mutant SCN5A gene and then administer the drug to be tested to the animal. The animal is then observed to determine whether torsade de pointes or ventricular fibrillation occurs. If no such adverse events occur then the drug will not induce them in persons with the mutation. If such events do occur in the transgenic animals but do not occur in animals expressing wild-type SCN5A when they are administered the drug, then the drugs can induce torsade depointes and ventricular fibrillation in persons with the SCN5A mutation as a result of the mutation.

Example 4

Generation of Polyclonal Antibody Against SCN5A

Segments of SCN5A coding sequence are expressed as fusion protein in *E. Coli*. The overexpressed protein is purified by gel elution and used to immunize rabbits and mice using a procedure similar to the one described by Harlow and Lane (1988). This procedure has been shown to generate Abs against various other proteins (for example, see Kraemer et al., 1993).

Briefly, a stretch of SCN5A coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the SCN5A fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the SCN5A gene product. These antibodies, in conjunction with antibodies to wild type SCN5A, are used to detect the presence and the relative level of the mutant forms in various tissues and biological fluids.

Example 5

Generation of Monoclonal Antibodies Specific for SCN5A

Monoclonal antibodies are generated according to the following protocol. Mice are immunized with immunogen comprising intact SCN5A or SCN5A peptides (wild type or mutant) conjugated to keyhole limpet hemocyanin using glutaraldehyde or EDC, as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein (1975). Briefly, P3.65.3 myeloma cells (American Type Culture Collection, Rockville, Md.) are fused with immune spleen cells using polyethylene glycol as described by Harlow and Lane (1988). Cells are plated at a density of $2 \times 10^5$ cells/well in 96 well tissue culture plates. Individual wells are examined for growth and the supernatants of wells with growth are tested for the presence of SCN5A specific antibodies by ELISA or RIA using wild type or mutant SCN5A target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

Example 6

Sandwich Assay for SCN5A

Monoclonal antibody is attached to a solid surface such as a plate, tube, bead or particle. Preferably, the antibody is attached to the well surface of a 96-well ELISA plate. 100 μL sample (e.g., serum, urine, tissue cytosol) containing the SCN5A peptide/protein (wild-type or mutants) is added to the solid phase antibody. The sample is incubated for 2 hrs at room temperature. Next the sample fluid is decanted, and the solid phase is washed with buffer to remove unbound material. 100 μL of a second monoclonal antibody (to a different determinant on SCN5A peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of SCN5A peptide/protein present in the sample, is quantified. Separate assays are performed using monoclonal antibodies which are specific for the wild-type SCN5A as well as monoclonal antibodies specific for each of the mutations identified in SCN5A.

Example 7

Assay to Screen Drugs Affecting the SCN5A Na$^+$ Channel

With the knowledge that SCN5A forms a cardiac sodium channel, it is now possible to devise an assay to screen for drugs which will have an effect on this channel. The gene SCN5A is transfected into oocytes or mammalian cells and expressed as described above. The transfection is performed using wild-type or specifically mutated SCN5A. When the gene used for transfection contains a mutation which causes predisposition to drug-induced torsade de pointes and ventricular fibrillation a change in the induced current is seen as compared to transfection with the wild-type gene. A drug candidate is added to the bathing solution of the transfected cells to test the effects of the drug candidates upon the induced current. A drug candidate, which alters the induced current such that it is closer to the current seen with cells transfected with wild-type SCN5A, is useful for treating drug-induced torsade de pointes and ventricular fibrillation.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul S F, et al. (1997). *Nucl. Acids Res.* 25:3389–3402.
Anand, R (1992). *Techniques for the Analysis of Complex Genomes*, (Academic Press).
Anderson W F, et al. (1980). *Proc. Natl. Acad. Sci. USA* 77:5399–5403.
Antzelevitch C and Sicouri S (1994). *J. Am. Col. Card.* 23:259–277.
Antzelevitch C, et al. (1999). *J. Electrocardiol.* 32 (Suppl. 1):158–165.
Attali B, et al. (1993). *Nature* 365:850–852.
Attwell D, et al. (1979). *Pflugers Arch.* 379:137–142.
Ausubel F M, et al. (1992). *Current Protocols in Molecular Biology*, (John Wiley & Sons, New York, N.Y.).
Bandyopadhyay P K and Temin H M (1984). *Mol. Cell. Biol.* 4:749–754.
Bartel P L, et al. (1993). "Using the 2-hybrid system to detect protein-protein interactions." In *Cellular Interactions in Development: A Practical Approach*, Oxford University Press, pp. 153–179.
Bazzett H (1920). *Heart* 7:353–370.
Beaucage S L and Caruthers M H (1981). *Tetra. Letts.* 22:1859–1862.
Berglund P, et al. (1993). *Biotechnology* 11:916–920.
Berkner K L, et al. (1988). *BioTechniques* 6:616–629.
Berkner K L (1992). *Curr. Top. Microbiol. Immunol.* 158: 39–66.
Borman S (1996). *Chemical & Engineering News*, December 9 issue, pp. 42–43.
Breakefield X O and Geller A I (1987). *Mol. Neurobiol.* 1:337–371.
Brinster R L, et al. (1981). *Cell* 27:223–231.
Bruggemann A, et al. (1993). *Nature* 365:445–448.
Buchschacher G L and Panganiban A T (1992). *J. Virol.* 66:2731–2739.
Busch A E, et al. (1992). *Science* 255:1705–1707.
Capecchi M R (1989). *Science* 244:1288.
Cardiac Arrhythmia Suppression Trial II Investigators (1992). *N. Engl. J. Med.* 327:227–233.
Cariello N F (1988). *Am. J. Human Genetics* 42:726–734.
Chee M, et al. (1996). *Science* 274:610–614.
Chevray P M and Nathans D N (1992). *Proc. NatL. Acad. Sci. USA* 89:5789–5793.
Compton J (1991). *Nature* 350:91–92.
Conner B J, et al. (1983). *Proc. Natl. Acad. Sci. USA* 80:278–282.
Costantini F and Lacy E (1981). *Nature* 294:92–94.
Cotten M, et al. (1990). *Proc. Natl. Acad. Sci. USA* 87:4033–4037.
Cotton R G, et al. (1988). *Proc. Natl. Acad. Sci. USA* 85:4397–4401.
Couderc J P, et al. (1999). *Pacing Clin. Electrophysiol.* 22:1581–1592.
Culver K W, et al. (1992). *Science* 256:1550–1552.
Culver K (1996). *Gene Therapy: A Primer for Physicians*, 2nd Ed., Mary Ann Liebert.
Curiel D T, et al. (1991). *Proc. Natl. Acad. Sci. USA* 88:8850–8854.
Curiel D T, et al. (1992). *Hum. Gene Ther.* 3:147–154.
Curran M E, et al. (1995). *Cell* 80:795–804.
DeRisi J, et al. (1996). *Nat. Genet.* 14:457–460.
Deschenes I, et al. (2000). *Cardiovasc. Res.* 46:55–65.

Deutscher M (1990). *Meth. Enzymology* 182:83–89 (Academic Press, San Diego, Calif.).
Donehower L A, et al. (1992). *Nature* 356:215.
Duggal P et al. (1998). *Circulation* 97:142–146.
Editorial (1996). *Nature Genetics* 14:367–370.
Elghanian R, et al. (1997). *Science* 277:1078–1081.
*Enhancers and Eukaryotic Gene Expression*, Cold Spring Harbor Press, Cold Spring Harbor, N.Y. (1983).
Erickson J, et al. (1990). *Science* 249:527–533.
Fahy E, et al. (1991). *PCR Methods Appl.* 1:25–33.
Felgner P L, et al. (1987). *Proc. Natl. Acad. Sci. USA* 84:7413–7417.
Fields S and Song O-K (1989). *Nature* 340:245–246.
Fiers W, et al. (1978). *Nature* 273:113–120.
Fink D J, et al. (1992). *Hum. Gene Ther.* 3:11–19.
Fink D J, et al. (1996). *Ann. Rev. Neurosci.* 19:265–287.
Finkelstein J, et al. (1990). *Genomics* 7:167–172.
Fodor S P A (1997). *Science* 277:393–395.
Freese A, et al. (1990). *Biochem. Pharmacol.* 40:2189–2199.
Friedman T (1991). In *Therapy for Genetic Diseases*, T. Friedman, ed., Oxford University Press, pp. 105–121.
Gellens M, et al. (1992). *Proc. Natl. Acad. Sci. USA* 89:554–558.
George A L, et al. (1995). *Cytogenet. Cell. Genet.* 68:67–70.
Glover D (1985). *DNA Cloning*, I and II (Oxford Press).
Goding (1986). *Monoclonal Antibodies: Principles and Practice*, 2d ed. (Academic Press, N.Y.).
Godowski P J, et al. (1988). *Science* 241:812–816.
Goldstein S A N and Miller C (1991). *Neuron* 7:403–408.
Gordon J W, et al. (1980). *Proc. Natl. Acad. Sci. USA* 77:7380–7384.
Gorziglia M and Kapikian A Z (1992). *J. Virol.* 66:4407–4412.
Graham F L and van der Eb AJ (1973). *Virology* 52:456–467.
Grompe M (1993). *Nature Genetics* 5:111–117.
Grompe M, et al. (1989). *Proc. Natl. Acad. Sci. USA* 86:5855–5892.
Guthrie G and Fink G R (1991). *Guide to Yeast Genetics and Molecular Biology* (Academic Press).
Hacia J G, et al. (1996). *Nature Genetics* 14:441–447.
Harlow E and Lane D (1988). *Antibodies: A Laboratory Manual* (Cold Spring Harbor Laboratory, Cold Spring Harbor, N.Y.).
Hasty P K, et al. (1991). *Nature* 350:243.
Hausdorff S F, et al. (1991). *Biochem.* 30:3341–3346.
Helseth E, et al. (1990). *J. Virol.* 64:2416–2420.
Hodgson J (1991). *Bio/Technology* 9:19–21.
Huse W D, et al. (1989). *Science* 246:1275–1281.
Innis M A, et al. (1990). *PCR Protocols: A Guide to Methods and Applications* (Academic Press, San Diego, Calif.).
Jablonski E, et al. (1986). *Nucl. Acids Res.* 14:6115–6128.
Jakoby W B and Pastan I H (eds.) (1979). Cell Culture. *Methods in Enzymology* Vol. 58 (Academic Press, Inc., Harcourt Brace Jovanovich (NY)).
January C T and Riddle J M (1989). *Circ. Res.* 64:977–990.
Jervell A and Lange-Nielsen F (1957). *Am. Heart J.* 54:59–68.
Jiang C, et al. (1994). *Nat. Genet.* 8:141–147.
Johnson P A, et al. (1992). *J. Virol.* 66:2952–2965.
Johnson, et al. (1993). "Peptide Turn Mimetics" in *Biotechnology and Pharmacy*, Pezzuto et al., eds., Chapman and Hall, New York.
Kambouris N G, et al. (2000). *J Clin. Invest.* 105:1133–1140.
Kaneda Y, et al. (1989). *J Biol. Chem.* 264:12126–12129.
Kanehisa M (1984). *Nucl. Acids Res.* 12:203–213.
Kannel W B, et al. (1987). *Am. Heart J.* 113:799–804.
Keating M T, et al. (1991a). *Science* 252:704–706.
Keating M T, et al. (1991b). *Am. J. Hum. Genet.* 49:1335–1339.
Kinszler K W, et al. (1991). *Science* 251:1366–1370.
Kohler G and Milstein C (1975). *Nature* 256:495–497.
Kraemer F B, et al. (1993). *J. Lipid Res.* 34:663–672.
Kubo T, et al. (1988). *FEBS Lett.* 241:119.
Kyte J and Doolittle RF (1982). *J. Mol. Biol.* 157:105–132.
Landegren U, et al. (1988). *Science* 242:229–237.
Lee J E, et al. (1995). *Science* 268:836–844.
Lesage F, et al. (1993). *Receptors and Channels* 1:143–152.
Lim C S, et al. (1991). *Circulation* 83:2007–2011.
Lipshutz R J, et al. (1995). *BioTechniques* 19:442–447.
Lockhart D J, et al. (1996). *Nature Biotechnology* 14:1675–1680.
Madzak C, et al. (1992). *J. Gen. Virol.* 73:1533–1536.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401–407.
Margolskee R F (1992). *Curr. Top. Microbiol. Immunol.* 158:67–95.
Martin R, et al. (1990). *BioTechniques* 2:762–768.
Matteucci M D and Caruthers M H (1981). *J. Am. Chem. Soc.* 103:3185.
Matthews J A and Kricka L J (1988). *Anal. Biochem.* 169:1.
Merrifield B (1963). *J. Am. Chem. Soc.* 85:2149–2156.
Metzger D, et al. (1988). *Nature* 334:31–36.
Mifflin T E (1989). *Clinical Chem.* 35:1819–1825.
Miller A D (1992). *Curr. Top. Microbiol. Immunol.* 158:1–24.
Miller A D, et al. (1985). *Mol. Cell. Biol.* 5:431–437.
Miller A D, et al. (1988). *J. Virol.* 62:4337–4345.
Modrich P (1991). *Ann. Rev. Genet.* 25:229–253.
Mombaerts P, et al. (1992). *Cell* 68:869.
Moss A J and McDonald J (1971). *N. Engl. J. Med.* 285:903–904.
Moss A J, et al. (1991). *Circulation* 84:1136–1144.
Moss B (1992). *Curr. Top. Microbiol. Immunol.* 158:25–38.
Moss B (1996). *Proc. Natl. Acad. Sci. USA* 93:11341–11348.
Muzyczka N (1992). *Curr. Top. Microbiol. Immunol.* 158:97–129.
Nabel E G, et al. (1990). *Science* 249:1285–1288.
Nabel (1992). *Hum. Gene Ther.* 3:399–410.
Naldini L, et al. (1996). *Science* 272:263–267.
Newton C R, et al. (1989). *Nucl. Acids Res.* 17:2503–2516.
Neyroud N, et al. (1997). *Nat. Genet.* 15:186–189.
Nguyen Q, et al. (1992). *BioTechniques* 13:116–123.
Novack D F, et al. (1986). *Proc. Natl. Acad. Sci. USA* 83:586–590.
Ohi S, et al. (1990). *Gene* 89:279–282.
Orita M, et al. (1989). *Proc. Natl. Acad. Sci. USA* 86:2766–2770.
Page K A, et al. (1990). *J. Virol.* 64:5270–5276.
Pellicer A, et al. (1980). *Science* 209:1414–1422.
Petropoulos C J, et al. (1992). *J. Virol.* 66:3391–3397.
Philpott K L, et al. (1992). *Science* 256:1448.
Quantin B, et al. (1992). *Proc. Natl. Acad. Sci. USA* 89:2581–2584.
*Remington's Pharmaceutical Sciences*, 18th Ed. (1990, Mack Publishing Co., Easton, Pa.).
Rigby P W J, et al. (1977). *J. Mol. Biol.* 113:237–251.
Romano C (1965). *Lancet* I658–659.
Romano C, et al. (1963). *Clin. Pediatr.* 45:656–683.
Rook M B, et al. (1999). *Cardiovasc. Res.* 44:507–517.

Rosenfeld M A, et al. (1992). *Cell* 68:143–155.
Ruano G and Kidd K K (1989). *Nucl. Acicls Res.* 17:8392.
Russell M W, et al. (1995). *Am. J. Hum. Genet.* 57:503–507.
Russell D and Hirata R (1998). *Nature Genetics* 18:323–328.
Sambrook J, et al. (1989). *Molecular Cloning: A Laboratory Manual*, 2nd Ed. (Cold Spring HarborLaboratory, Cold Spring Harbor, N.Y.).
Sanguinetti M C, et al. (1996). *Nature* 384:80–83.
Scharf S J, et al. (1986). *Science* 233:1076–1078.
Schneider G, et al. (1998). *Nature Genetics* 18:180–183.
Schott J, et al. (1995). *Am. J. Hum. Genet.* 57:1114–1122.
Schultze-Bahr E, et al. (1997). *Nat. Genet.* 17:267–268.
Schwartz P J, et al. (1975). *Am. Heart J.* 109:378–390.
Schwartz P J, et al. (1994). "The long QT syndrome." In *Cardiac Electrophysiology: from cell to bedside.* D. P. Zipes and J. Jalife eds. (W. B. Sanders Company) pp.788–811.
Scopes R (1982). *Protein Purification: Principles and Practice*, (Springer-Verlag, N.Y.).
Sheffield V C, et al. (1989). *Proc. Natl. Acad. Sci. USA* 86:232–236.
Sheffield V C, et al. (1991). *Am. J. Hum. Genet.* 49:699–706.
Shenk T E, et al. (1975). *Proc. Natl. Acad. Sci. USA* 72:989–993.
Shimada T, et al. (1991). *J. Clin. Invest.* 88:1043–1047.
Shinkai Y, et al. (1992). *Cell* 68:855.
Shoemaker D D, et al. (1996). *Nature Genetics* 14:450–456.
Snouwaert J N, et al. (1992). *Science* 257:1083.
Sorge J, et al. (1984). *Mol. Cell. Biol.* 4:1730–1737.
Spargo C A, et al. (1996). *Mol. Cell. Probes* 10:247–256.
Splawski I, et al. (1997a). *N. Engl. J. Med.* 336:1562–1567.
Splawski I, et al. (1997b). *Nat. Genet.* 17:338–340.
Stewart M J, et al. (1992). *Hum. Gene Ther.* 3:267–275.
Stratford-Perricaudet L D, et al. (1990). *Hum. Gene Ther.* 1:241–256.
SurawiczB (1989). *J. Am. Coll. Cardiol.* 14:172–184.
Takumi T, et al. (1988). *Science* 242:1042–1045.
Takumi T, et al. (1991). *J. Biol. Chem.* 266:22192–22198.
Tyson J, et al. (1997). *Hum. Mol. Genet.* 6:2179–2185.
Valancius V and Smithies O (1991). *Mol. Cell Biol.* 11:1402.
Veldkamp M W, et al. (2000). *Circ. Res.* 12:E91-E97.
Vetter D E, et al. (1996). *Neuron* 17:1251–1264.
Vincent G M, et al. (1992). *N. Engl. J. Med.* 327:846–852.
Wagner E, et al. (1991). *Proc. Natl. Acad. Sci. USA* 88:4255–4259.
Wagner E, et al. (1990). *Proc. Natl. Acad. Sci. USA* 87:3410–3414.
Walker G T, et al., (1992). *Nucl. Acids Res.* 20:1691–1696.
Wang C Y and Huang L (1989). *Biochemistry* 28:9508–9514.
Wang D W, et al. (1996). *Proc. Natl. Acad. Sci. USA* 93:13200–13205.
Wang K W and Goldstein S A (1995). *Neuron* 14:1303–1309.
Wang K W, et al. (1996). *Neuron* 16:571–577.
Wang Q, et al. (1995). *Cell* 80:805–811.
Wang Q, et al. (1996). *Nat. Genet.* 12:17–23.
Ward O C (1964). *J. Ir. Med. Assoc.* 54:103–106.
Warmke J E and Ganetzky B (1994). *Proc. Natl. Acad. Sci.* 91:3438–3442.
Wartell R M, et al. (1990). *Nucl. Acids Res.* 18:2699–2705.
Wells J A (1991). *Methods Enzymol.* 202:390–411.
Wetmur J G and Davidson N (1968). *J. Mol. Biol.* 31:349–370.
White M B, et al. (1992). *Genomics* 12:301–306.
White R and Lalouel J M (1988). *Annu. Rev. Genet.* 22:259–279.
Wilkinson G W and Akrigg A (1992). *Nucleic Acids Res.* 20:2233–2239.
Willich S N, et al. (1987). Am. J. Cardiol. 60:801–806.
Wolff J A, et al. (1990). Science 247:1465–1468.
Wolff J A, et al. (1991). *BioTechniques* 11:474–485.
Wu D Y and Wallace R B (1989). *Genomics* 4:560–569.
Wu C H, et al. (1989). *J. Biol. Chem.* 264:16985–16987.
Wu G Y, et al. (1991). *J. Biol. Chem.* 266:14338–14342.
Zenke M, et al. (1990). *Proc. Natl. Acad. Sci. USA* 87:3655–3659.
Zipes D P (1987). *Am. J. Cardiol.* 59:26E-31E.

Patents and Patent Applications:
European Patent Application Publication No. 0332435.
EPO Publication No. 225,807.
Hitzeman et al., EP 73,675A.
EP 425,731A.
WO 84/03564.
WO 90/07936.
WO 92/19195.
WO 93/07282.
WO 94/25503.
WO 95/01203.
WO 95/05452.
WO 96/02286.
WO 96/02646.
WO 96/11698.
WO 96/40871.
WO 96/40959.
WO 97/02048.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,554,101.
U.S. Pat. No. 4,683,195.
U.S. Pat. No. 4,683,202.
U.S. Pat. No. 4,816,567.
U.S. Pat. No. 4,868,105.
U.S. Pat. No. 5,252,479.
U.S. Pat. No. 5,270,184.
U.S. Pat. No. 5,409,818.
U.S. Pat. No. 5,436,146.
U.S. Pat. No. 5,455,166.
U.S. Pat. No. 5,550,050.
U.S. Pat. No. 5,691,198.
U.S. Pat. No. 5,735,500.
U.S. Pat. No. 5,747,469.
U.S. Pat. No. 5,846,710.
U.S. Pat. No. 5,856,092.
U.S. Pat. No. 5,888,819.
U.S. Pat. No. 6,004,744.

What is claimed is:

1. A method for diagnosing the presence of a polymorphism in human SCN5A which causes predisposition to drug-induced torsade de pointes or ventricular fibrillation wherein said method comprises determining the presence of said polymorphism in a sample from a human by means which detect the presence of said polymorphism, wherein said polymorphism is one which results in SCN5A encoding the polypeptide of SEQ ID NO:4 and wherein the presence of said polymorphism is indicative of said predisposition.

2. The method of claim 1 wherein said means comprises:
   a) using a single-stranded conformation polymorphism technique to assay for said polymorphism;
   b) sequencing human SCN5A;
   c) performing an RNAse assay;
   d) performing an allele specific hybridization;
   e) performing a single base extension assay;
   f) performing an allele specific polymerase chain reaction;
   g) amplifying all or part of the SCN5A gene from said sample to produce an amplified sequence and sequencing the amplified sequence;
   h) molecularly cloning all or part of the SCN5A gene from said sample to produce a cloned sequence and sequencing the cloned sequence;
   i) amplification of SCN5A gene sequences in said sample and hybridization of the amplified sequences to nucleic acid probes which comprise wild-type SCN5A gene sequences;
   j) amplification of SCN5A gene sequences in said sample and hybridization of the amplified sequences to nucleic acid probes which comprise mutant SCN5A gene sequences; or
   k) determining in situ hybridization of the SCN5A gene from said sample with one or more nucleic acid probes which comprise the SCN5A gene sequence or a mutant SCN5A gene sequence.

3. An isolated DNA comprising a nucleic acid encoding the polypeptide of SEQ ID NO:4.

4. An isolated polypeptide of SEQ ID NO:4.

5. A cell transfected with the DNA of claim 1, wherein the cell is an isolated cell or a cell in culture.

6. A vector comprising the isolated DNA of claim 1.

7. A cell transfected with the vector of claim 6, wherein the cell is an isolated cell or a cell in culture.

* * * * *

SEQUENCE LISTING

<160> NUMBER OF SEQ ID NOS: 6

<210> SEQ ID NO 1
<211> LENGTH: 8491
<212> TYPE: DNA
<213> ORGANISM: Homo sapiens
<220> FEATURE:
<221> NAME/KEY: CDS
<222> LOCATION: (151)..(6198)
<220> FEATURE:
<221> NAME/KEY: misc_feature
<222> LOCATION: (1)..(8491)
<223> OTHER INFORMATION: n may be any base

<400> SEQUENCE: 1

```
gccgctgagc ctgcgcccag tgccccgagc ccgcgccga gccgagtccg cgccaagcag      60
cagccgccca cccgggggcc cggccggggg accagcagct tccccacagg caacgtgagg     120
agagcctgtg cccagaagca ggatgagaag atg gca aac ttc cta tta cct cgg     174
                                 Met Ala Asn Phe Leu Leu Pro Arg
                                  1               5 ggc acc agc agc ttc cgc agg ttc aca cgg gag tcc ctg gca gcc atc      222
Gly Thr Ser Ser Phe Arg Arg Phe Thr Arg Glu Ser Leu Ala Ala Ile
         10                  15                  20 gag aag cgc atg gcg gag aag caa gcc cgc ggc tca acc acc ttg cag      270
Glu Lys Arg Met Ala Glu Lys Gln Ala Arg Gly Ser Thr Thr Leu Gln
 25                  30                  35                  40 gag agc cga gag ggg ctg ccc gag gag gag gct ccc cgg ccc cag ctg      318
Glu Ser Arg Glu Gly Leu Pro Glu Glu Glu Ala Pro Arg Pro Gln Leu
                 45                  50                  55 gac ctg cag gcc tcc aaa aag ctg cca gat ctc tat ggc aat cca ccc      366
Asp Leu Gln Ala Ser Lys Lys Leu Pro Asp Leu Tyr Gly Asn Pro Pro
             60                  65                  70 caa gag ctc atc gga gag ccc ctg gag gac ctg gac ccc ttc tat agc      414
Gln Glu Leu Ile Gly Glu Pro Leu Glu Asp Leu Asp Pro Phe Tyr Ser
         75                  80                  85 acc caa aag act ttc atc gta ctg aat aaa ggc aag acc atc ttc cgg      462
Thr Gln Lys Thr Phe Ile Val Leu Asn Lys Gly Lys Thr Ile Phe Arg
     90                  95                 100 ttc agt gcc acc aac gcc ttg tat gtc ctc agt ccc ttc cac cca gtt      510
Phe Ser Ala Thr Asn Ala Leu Tyr Val Leu Ser Pro Phe His Pro Val
105                 110                 115                 120 cgg aga gcg gct gtg aag att ctg gtt cac tcg ctc ttc aac atg ctc      558
Arg Arg Ala Ala Val Lys Ile Leu Val His Ser Leu Phe Asn Met Leu
                125                 130                 135 atc atg tgc acc atc ctc acc aac tgc gtg ttc atg gcc cag cac gac      606
Ile Met Cys Thr Ile Leu Thr Asn Cys Val Phe Met Ala Gln His Asp
            140                 145                 150 cct cca ccc tgg acc aag tat gtc gag tac acc ttc acc gcc att tac      654
Pro Pro Pro Trp Thr Lys Tyr Val Glu Tyr Thr Phe Thr Ala Ile Tyr
        155                 160                 165 acc ttt gag tct ctg gtc aag att ctg gct cga gct ttc tgc ctg cac      702
Thr Phe Glu Ser Leu Val Lys Ile Leu Ala Arg Ala Phe Cys Leu His
    170                 175                 180 gcg ttc act ttc ctt cgg gac cca tgg aac tgg ctg gac ttt agt gtg      750
Ala Phe Thr Phe Leu Arg Asp Pro Trp Asn Trp Leu Asp Phe Ser Val
185                 190                 195                 200 att atc atg gca tac aca act gaa ttt gtg gac ctg ggc aat gtc tca      798
Ile Ile Met Ala Tyr Thr Thr Glu Phe Val Asp Leu Gly Asn Val Ser
                205                 210                 215
```

-continued

```
gcc tta cgc acc ttc cga gtc ctc cgg gcc ctg aaa act ata tca gtc    846
Ala Leu Arg Thr Phe Arg Val Leu Arg Ala Leu Lys Thr Ile Ser Val
            220                 225                 230 att tca ggg ctg aag acc atc gtg ggg gcc ctg atc cag tct gtg aag    894
Ile Ser Gly Leu Lys Thr Ile Val Gly Ala Leu Ile Gln Ser Val Lys
        235                 240                 245 aag ctg gct gat gtg atg gtc ctc aca gtc ttc tgc ctc agc gtc ttt    942
Lys Leu Ala Asp Val Met Val Leu Thr Val Phe Cys Leu Ser Val Phe
250                 255                 260 gcc ctc atc ggc ctg cag ctc ttc atg ggc aac cta agg cac aag tgt    990
Ala Leu Ile Gly Leu Gln Leu Phe Met Gly Asn Leu Arg His Lys Cys
265                 270                 275                 280 gtg cgc aac ttc aca gcg ctc aac ggc acc aac ggc tcc gtg gag gcc   1038
Val Arg Asn Phe Thr Ala Leu Asn Gly Thr Asn Gly Ser Val Glu Ala
                285                 290                 295 gac ggc ttg gtc tgg gaa tcc ctg gac ctt tac ctc agt gat cca gaa   1086
Asp Gly Leu Val Trp Glu Ser Leu Asp Leu Tyr Leu Ser Asp Pro Glu
            300                 305                 310 aat tac ctg ctc aag aac ggc acc tct gat gtg tta ctg tgt ggg aac   1134
Asn Tyr Leu Leu Lys Asn Gly Thr Ser Asp Val Leu Leu Cys Gly Asn
        315                 320                 325 agc tct gac gct ggg aca tgt ccg gag ggc tac cgg tgc cta aag gca   1182
Ser Ser Asp Ala Gly Thr Cys Pro Glu Gly Tyr Arg Cys Leu Lys Ala
330                 335                 340 ggc gag aac ccc gac cac ggc tac acc agc ttc gat tcc ttt gcc tgg   1230
Gly Glu Asn Pro Asp His Gly Tyr Thr Ser Phe Asp Ser Phe Ala Trp
345                 350                 355                 360 gcc ttt ctt gca ctc ttc cgc ctg atg acg cag gac tgc tgg gag cgc   1278
Ala Phe Leu Ala Leu Phe Arg Leu Met Thr Gln Asp Cys Trp Glu Arg
                365                 370                 375 ctc tat cag cag acc ctc agg tcc gca ggg aag atc tac atg atc ttc   1326
Leu Tyr Gln Gln Thr Leu Arg Ser Ala Gly Lys Ile Tyr Met Ile Phe
            380                 385                 390 ttc atg ctt gtc atc ttc ctg ggg tcc ttc tac ctg gtg aac ctg atc   1374
Phe Met Leu Val Ile Phe Leu Gly Ser Phe Tyr Leu Val Asn Leu Ile
        395                 400                 405 ctg gcc gtg gtc gca atg gcc tat gag gag caa aac caa gcc acc atc   1422
Leu Ala Val Val Ala Met Ala Tyr Glu Glu Gln Asn Gln Ala Thr Ile
410                 415                 420 gct gag acc gag gag aag gaa aag cgc ttc cag gag gcc atg gaa atg   1470
Ala Glu Thr Glu Glu Lys Glu Lys Arg Phe Gln Glu Ala Met Glu Met
425                 430                 435                 440 ctc aag aaa gaa cac gag gcc ctc acc atc agg ggt gtg gat acc gtg   1518
Leu Lys Lys Glu His Glu Ala Leu Thr Ile Arg Gly Val Asp Thr Val
                445                 450                 455 tcc cgt agc tcc ttg gag atg tcc cct ttg gcc cca gta aac agc cat   1566
Ser Arg Ser Ser Leu Glu Met Ser Pro Leu Ala Pro Val Asn Ser His
            460                 465                 470 gag aga aga agc aag agg aga aaa cgg atg tct tca gga act gag gag   1614
Glu Arg Arg Ser Lys Arg Arg Lys Arg Met Ser Ser Gly Thr Glu Glu
        475                 480                 485 tgt ggg gag gac agg ctc ccc aag tct gac tca gaa gat ggt ccc aga   1662
Cys Gly Glu Asp Arg Leu Pro Lys Ser Asp Ser Glu Asp Gly Pro Arg
490                 495                 500 gca atg aat cat ctc agc ctc acc cgt ggc ctc agc agg act tct atg   1710
Ala Met Asn His Leu Ser Leu Thr Arg Gly Leu Ser Arg Thr Ser Met
505                 510                 515                 520 aag cca cgt tcc agc cgc ggg agc att ttc acc ttt cgc agg cga gac   1758
Lys Pro Arg Ser Ser Arg Gly Ser Ile Phe Thr Phe Arg Arg Arg Asp
                525                 530                 535
```

-continued

| | |
|---|---|
| ctg ggt tct gaa gca gat ttt gca gat gat gaa aac agc aca gcg cgg<br>Leu Gly Ser Glu Ala Asp Phe Ala Asp Asp Glu Asn Ser Thr Ala Arg<br>540           545                 550 | 1806 |
| gag agc gag agc cac cac aca tca ctg ctg gtg ccc tgg ccc ctg cgc<br>Glu Ser Glu Ser His His Thr Ser Leu Leu Val Pro Trp Pro Leu Arg<br>    555                 560                 565 | 1854 |
| cgg acc agt gcc cag gga cag ccc agt ccc gga acc tcg gct cct ggc<br>Arg Thr Ser Ala Gln Gly Gln Pro Ser Pro Gly Thr Ser Ala Pro Gly<br>570                 575                 580 | 1902 |
| cac gcc ctc cat ggc aaa aag aac agc act gtg gac tgc aat ggg gtg<br>His Ala Leu His Gly Lys Lys Asn Ser Thr Val Asp Cys Asn Gly Val<br>585                 590                 595                 600 | 1950 |
| gtc tca tta ctg ggg gca ggc gac cca gag gcc aca tcc cca gga agc<br>Val Ser Leu Leu Gly Ala Gly Asp Pro Glu Ala Thr Ser Pro Gly Ser<br>            605                 610                 615 | 1998 |
| cac ctc ctc cgc cct gtg atg cta gag cac ccg cca gac acg acc acg<br>His Leu Leu Arg Pro Val Met Leu Glu His Pro Pro Asp Thr Thr Thr<br>        620                 625                 630 | 2046 |
| cca tcg gag gag cca ggc ggc ccc cag atg ctg acc tcc cag gct ccg<br>Pro Ser Glu Glu Pro Gly Gly Pro Gln Met Leu Thr Ser Gln Ala Pro<br>    635                 640                 645 | 2094 |
| tgt gta gat ggc ttc gag gag cca gga gca cgg cag cgg gcc ctc agc<br>Cys Val Asp Gly Phe Glu Glu Pro Gly Ala Arg Gln Arg Ala Leu Ser<br>650                 655                 660 | 2142 |
| gca gtc agc gtc ctc aca agc gca ctg gaa gag tta gag gag tct cgc<br>Ala Val Ser Val Leu Thr Ser Ala Leu Glu Glu Leu Glu Glu Ser Arg<br>665                 670                 675                 680 | 2190 |
| cac aag tgt cca cca tgc tgg aac cgt ctc gcc cag cgc tac ctg atc<br>His Lys Cys Pro Pro Cys Trp Asn Arg Leu Ala Gln Arg Tyr Leu Ile<br>            685                 690                 695 | 2238 |
| tgg gag tgc tgc ccg ctg tgg atg tcc atc aag cag gga gtg aag ttg<br>Trp Glu Cys Cys Pro Leu Trp Met Ser Ile Lys Gln Gly Val Lys Leu<br>        700                 705                 710 | 2286 |
| gtg gtc atg gac ccg ttt act gac ctc acc atc act atg tgc atc gta<br>Val Val Met Asp Pro Phe Thr Asp Leu Thr Ile Thr Met Cys Ile Val<br>    715                 720                 725 | 2334 |
| ctc aac aca ctc ttc atg gcg ctg gag cac tac aac atg aca agt gaa<br>Leu Asn Thr Leu Phe Met Ala Leu Glu His Tyr Asn Met Thr Ser Glu<br>730                 735                 740 | 2382 |
| ttc gag gag atg ctg cag gtc gga aac ctg gtc ttc aca ggg att ttc<br>Phe Glu Glu Met Leu Gln Val Gly Asn Leu Val Phe Thr Gly Ile Phe<br>745                 750                 755                 760 | 2430 |
| aca gca gag atg acc ttc aag atc att gcc ctc gac ccc tac tac tac<br>Thr Ala Glu Met Thr Phe Lys Ile Ile Ala Leu Asp Pro Tyr Tyr Tyr<br>            765                 770                 775 | 2478 |
| ttc caa cag ggc tgg aac atc ttc gac agc atc atc gtc atc ctt agc<br>Phe Gln Gln Gly Trp Asn Ile Phe Asp Ser Ile Ile Val Ile Leu Ser<br>        780                 785                 790 | 2526 |
| ctc atg gag ctg ggc ctg tcc cgc atg agc aac ttg tcg gtg ctg cgc<br>Leu Met Glu Leu Gly Leu Ser Arg Met Ser Asn Leu Ser Val Leu Arg<br>    795                 800                 805 | 2574 |
| tcc ttc cgc ctg ctg cgg gtc ttc aag ctg gcc aaa tca tgg ccc acc<br>Ser Phe Arg Leu Leu Arg Val Phe Lys Leu Ala Lys Ser Trp Pro Thr<br>810                 815                 820 | 2622 |
| ctg aac aca ctc atc aag atc atc ggg aac tca gtg ggg gca ctg ggg<br>Leu Asn Thr Leu Ile Lys Ile Ile Gly Asn Ser Val Gly Ala Leu Gly<br>825                 830                 835                 840 | 2670 |
| aac ctg aca ctg gtg cta gcc atc atc gtg ttc atc ttt gct gtg gtg<br>Asn Leu Thr Leu Val Leu Ala Ile Ile Val Phe Ile Phe Ala Val Val | 2718 |

-continued

```
                    845                 850                 855
ggc atg cag ctc ttt ggc aag aac tac tcg gag ctg agg gac agc gac       2766
Gly Met Gln Leu Phe Gly Lys Asn Tyr Ser Glu Leu Arg Asp Ser Asp
            860                 865                 870 tca ggc ctg ctg cct cgc tgg cac atg atg gac ttc ttt cat gcc ttc       2814
Ser Gly Leu Leu Pro Arg Trp His Met Met Asp Phe Phe His Ala Phe
        875                 880                 885 cta atc atc ttc cgc atc ctc tgt gga gag tgg atc gag acc atg tgg       2862
Leu Ile Ile Phe Arg Ile Leu Cys Gly Glu Trp Ile Glu Thr Met Trp
    890                 895                 900 gac tgc atg gag gtg tcg ggg cag tca tta tgc ctg ctg gtc ttc ttg       2910
Asp Cys Met Glu Val Ser Gly Gln Ser Leu Cys Leu Leu Val Phe Leu
905                 910                 915                 920 ctt gtt atg gtc att ggc aac ctt gtg gtc ctg aat ctc ttc ctg gcc       2958
Leu Val Met Val Ile Gly Asn Leu Val Val Leu Asn Leu Phe Leu Ala
                925                 930                 935 ttg ctg ctc agc tcc ttc agt gca gac aac ctc aca gcc cct gat gag       3006
Leu Leu Leu Ser Ser Phe Ser Ala Asp Asn Leu Thr Ala Pro Asp Glu
            940                 945                 950 gac aga gag atg aac aac ctc cag ctg gcc ctg gcc cgc atc cag agg       3054
Asp Arg Glu Met Asn Asn Leu Gln Leu Ala Leu Ala Arg Ile Gln Arg
        955                 960                 965 ggc ctg cgc ttt gtc aag cgg acc acc tgg gat ttc tgc tgt ggt ctc       3102
Gly Leu Arg Phe Val Lys Arg Thr Thr Trp Asp Phe Cys Cys Gly Leu
    970                 975                 980 ctg cgg cac cgg cct cag aag ccc gca gcc ctt gcc gcc cag ggc cag       3150
Leu Arg His Arg Pro Gln Lys Pro Ala Ala Leu Ala Ala Gln Gly Gln
985                 990                 995                 1000 ctg ccc agc tgc att  gcc acc ccc tac tcc  ccg cca ccc cca gag           3195
Leu Pro Ser Cys Ile  Ala Thr Pro Tyr Ser  Pro Pro Pro Glu
                1005                1010                1015 acg gag aag gtg cct  ccc acc cgc aag gaa  aca cag ttt gag gaa           3240
Thr Glu Lys Val Pro  Pro Thr Arg Lys Glu  Thr Gln Phe Glu Glu
            1020                1025                1030 ggc gag caa cca ggc  cag ggc acc ccc ggg  gat cca gag ccc gtg           3285
Gly Glu Gln Pro Gly  Gln Gly Thr Pro Gly  Asp Pro Glu Pro Val
        1035                1040                1045 tgt gtg ccc atc gct  gtg gcc gag tca gac  aca gat gac caa gaa           3330
Cys Val Pro Ile Ala  Val Ala Glu Ser Asp  Thr Asp Asp Gln Glu
    1050                1055                1060 gag gat gag gag aac  agc ctg ggc acg gag  gag gag tcc agc aag           3375
Glu Asp Glu Glu Asn  Ser Leu Gly Thr Glu  Glu Glu Ser Ser Lys
1065                1070                1075 cag cag gaa tcc cag  cct gtg tcc ggc tgg  ccc aga ggc cct ccg           3420
Gln Gln Glu Ser Gln  Pro Val Ser Gly Trp  Pro Arg Gly Pro Pro
                1080                1085                1090 gat tcc agg acc tgg  agc cag gtg tca gcg  act gcc tcc tct gag           3465
Asp Ser Arg Thr Trp  Ser Gln Val Ser Ala  Thr Ala Ser Ser Glu
            1095                1100                1105 gcc gag gcc agt gca  tct cag gcc gac tgg  cgg cag cag tgg aaa           3510
Ala Glu Ala Ser Ala  Ser Gln Ala Asp Trp  Arg Gln Gln Trp Lys
        1110                1115                1120 gcg gaa ccc cag gcc  cca ggg tgc ggt gag  acc cca gag gac agt           3555
Ala Glu Pro Gln Ala  Pro Gly Cys Gly Glu  Thr Pro Glu Asp Ser
    1125                1130                1135 tgc tcc gag ggc agc  aca gca gac atg acc  aac acc gct gag ctc           3600
Cys Ser Glu Gly Ser  Thr Ala Asp Met Thr  Asn Thr Ala Glu Leu
                1140                1145                1150 ctg gag cag atc cct  gac ctc ggc cag gat  gtc aag gac cca gag           3645
Leu Glu Gln Ile Pro  Asp Leu Gly Gln Asp  Val Lys Asp Pro Glu
```

```
                                                      -continued

Leu Glu Gln Ile Pro    Asp Leu Gly Gln Asp    Val Lys Asp Pro Glu
        1155                    1160                   1165 gac tgc ttc act gaa    ggc tgt gtc cgg cgc    tgt ccc tgc tgt gcg                3690
Asp Cys Phe Thr Glu    Gly Cys Val Arg Arg    Cys Pro Cys Cys Ala
        1170                    1175                   1180 gtg gac acc aca cag    gcc cca ggg aag gtc    tgg tgg cgg ttg cgc                3735
Val Asp Thr Thr Gln    Ala Pro Gly Lys Val    Trp Trp Arg Leu Arg
        1185                    1190                   1195 aag acc tgc tac cac    atc gtg gag cac agc    tgg ttc gag aca ttc                3780
Lys Thr Cys Tyr His    Ile Val Glu His Ser    Trp Phe Glu Thr Phe
        1200                    1205                   1210 atc atc ttc atg atc    cta ctc agc agt gga    gcg ctg gcc ttc gag                3825
Ile Ile Phe Met Ile    Leu Leu Ser Ser Gly    Ala Leu Ala Phe Glu
        1215                    1220                   1225 gac atc tac cta gag    gag cgg aag acc atc    aag gtt ctg ctt gag                3870
Asp Ile Tyr Leu Glu    Glu Arg Lys Thr Ile    Lys Val Leu Leu Glu
        1230                    1235                   1240 tat gcc gac aag atg    ttc aca tat gtc ttc    gtg ctg gag atg ctg                3915
Tyr Ala Asp Lys Met    Phe Thr Tyr Val Phe    Val Leu Glu Met Leu
        1245                    1250                   1255 ctc aag tgg gtg gcc    tac ggc ttc aag aag    tac ttc acc aat gcc                3960
Leu Lys Trp Val Ala    Tyr Gly Phe Lys Lys    Tyr Phe Thr Asn Ala
        1260                    1265                   1270 tgg tgc tgg ctc gac    ttc ctc atc gta gac    gtc tct ctg gtc agc                4005
Trp Cys Trp Leu Asp    Phe Leu Ile Val Asp    Val Ser Leu Val Ser
        1275                    1280                   1285 ctg gtg gcc aac acc    ctg ggc ttt gcc gag    atg ggc ccc atc aag                4050
Leu Val Ala Asn Thr    Leu Gly Phe Ala Glu    Met Gly Pro Ile Lys
        1290                    1295                   1300 tca ctg cgg acg ctg    cgt gca ctc cgt cct    ctg aga gct ctg tca                4095
Ser Leu Arg Thr Leu    Arg Ala Leu Arg Pro    Leu Arg Ala Leu Ser
        1305                    1310                   1315 cga ttt gag ggc atg    agg gtg gtg gtc aat    gcc ctg gtg ggc gcc                4140
Arg Phe Glu Gly Met    Arg Val Val Val Asn    Ala Leu Val Gly Ala
        1320                    1325                   1330 atc ccg tcc atc atg    aac gtc ctc ctc gtc    tgc ctc atc ttc tgg                4185
Ile Pro Ser Ile Met    Asn Val Leu Leu Val    Cys Leu Ile Phe Trp
        1335                    1340                   1345 ctc atc ttc agc atc    atg ggc gtg aac ctc    ttt gcg ggg aag ttt                4230
Leu Ile Phe Ser Ile    Met Gly Val Asn Leu    Phe Ala Gly Lys Phe
        1350                    1355                   1360 ggg agg tgc atc aac    cag aca gag gga gac    ttg cct ttg aac tac                4275
Gly Arg Cys Ile Asn    Gln Thr Glu Gly Asp    Leu Pro Leu Asn Tyr
        1365                    1370                   1375 acc atc gtg aac aac    aag agc cag tgt gag    tcc ttg aac ttg acc                4320
Thr Ile Val Asn Asn    Lys Ser Gln Cys Glu    Ser Leu Asn Leu Thr
        1380                    1385                   1390 gga gaa ttg tac tgg    acc aag gtg aaa gtc    aac ttt gac aac gtg                4365
Gly Glu Leu Tyr Trp    Thr Lys Val Lys Val    Asn Phe Asp Asn Val
        1395                    1400                   1405 ggg gcc ggg tac ctg    gcc ctt ctg cag gtg    gca aca ttt aaa ggc                4410
Gly Ala Gly Tyr Leu    Ala Leu Leu Gln Val    Ala Thr Phe Lys Gly
        1410                    1415                   1420 tgg atg gac att atg    tat gca gct gtg gac    tcc agg ggg tat gaa                4455
Trp Met Asp Ile Met    Tyr Ala Ala Val Asp    Ser Arg Gly Tyr Glu
        1425                    1430                   1435 gag cag cct cag tgg    gaa tac aac ctc tac    atg tac atc tat ttt                4500
Glu Gln Pro Gln Trp    Glu Tyr Asn Leu Tyr    Met Tyr Ile Tyr Phe
        1440                    1445                   1450
```

-continued

| | | | | |
|---|---|---|---|---|
| gtc att ttc atc atc<br>Val Ile Phe Ile Ile<br>1455 | ttt ggg tct ttc ttc<br>Phe Gly Ser Phe Phe<br>1460 | acc ctg aac ctc ttt<br>Thr Leu Asn Leu Phe<br>1465 | | 4545 |
| att ggt gtc atc att<br>Ile Gly Val Ile Ile<br>1470 | gac aac ttc aac caa<br>Asp Asn Phe Asn Gln<br>1475 | cag aag aaa aag tta<br>Gln Lys Lys Lys Leu<br>1480 | | 4590 |
| ggg ggc cag gac atc<br>Gly Gly Gln Asp Ile<br>1485 | ttc atg aca gag gag<br>Phe Met Thr Glu Glu<br>1490 | cag aag aag tac tac<br>Gln Lys Lys Tyr Tyr<br>1495 | | 4635 |
| aat gcc atg aag aag<br>Asn Ala Met Lys Lys<br>1500 | ctg ggc tcc aag aag<br>Leu Gly Ser Lys Lys<br>1505 | ccc cag aag ccc atc<br>Pro Gln Lys Pro Ile<br>1510 | | 4680 |
| cca cgg ccc ctg aac<br>Pro Arg Pro Leu Asn<br>1515 | aag tac cag ggc ttc<br>Lys Tyr Gln Gly Phe<br>1520 | ata ttc gac att gtg<br>Ile Phe Asp Ile Val<br>1525 | | 4725 |
| acc aag cag gcc ttt<br>Thr Lys Gln Ala Phe<br>1530 | gac gtc acc atc atg<br>Asp Val Thr Ile Met<br>1535 | ttt ctg atc tgc ttg<br>Phe Leu Ile Cys Leu<br>1540 | | 4770 |
| aat atg gtg acc atg<br>Asn Met Val Thr Met<br>1545 | atg gtg gag aca gat<br>Met Val Glu Thr Asp<br>1550 | gac caa agt cct gag<br>Asp Gln Ser Pro Glu<br>1555 | | 4815 |
| aaa atc aac atc ttg<br>Lys Ile Asn Ile Leu<br>1560 | gcc aag atc aac ctg<br>Ala Lys Ile Asn Leu<br>1565 | ctc ttt gtg gcc atc<br>Leu Phe Val Ala Ile<br>1570 | | 4860 |
| ttc aca ggc gag tgt<br>Phe Thr Gly Glu Cys<br>1575 | att gtc aag ctg gct<br>Ile Val Lys Leu Ala<br>1580 | gcc ctg cgc cac tac<br>Ala Leu Arg His Tyr<br>1585 | | 4905 |
| tac ttc acc aac agc<br>Tyr Phe Thr Asn Ser<br>1590 | tgg aat atc ttc gac<br>Trp Asn Ile Phe Asp<br>1595 | ttc gtg gtt gtc atc<br>Phe Val Val Val Ile<br>1600 | | 4950 |
| ctc tcc atc gtg ggc<br>Leu Ser Ile Val Gly<br>1605 | act gtg ctc tcg gac<br>Thr Val Leu Ser Asp<br>1610 | atc atc cag aag tac<br>Ile Ile Gln Lys Tyr<br>1615 | | 4995 |
| ttc ttc tcc ccg acg<br>Phe Phe Ser Pro Thr<br>1620 | ctc ttc cga gtc atc<br>Leu Phe Arg Val Ile<br>1625 | cgc ctg gcc cga ata<br>Arg Leu Ala Arg Ile<br>1630 | | 5040 |
| ggc cgc atc ctc aga<br>Gly Arg Ile Leu Arg<br>1635 | ctg atc cga ggg gcc<br>Leu Ile Arg Gly Ala<br>1640 | aag ggg atc cgc acg<br>Lys Gly Ile Arg Thr<br>1645 | | 5085 |
| ctg ctc ttt gcc ctc<br>Leu Leu Phe Ala Leu<br>1650 | atg atg tcc ctg cct<br>Met Met Ser Leu Pro<br>1655 | gcc ctc ttc aac atc<br>Ala Leu Phe Asn Ile<br>1660 | | 5130 |
| ggg ctg ctg ctc ttc<br>Gly Leu Leu Leu Phe<br>1665 | ctc gtc atg ttc atc<br>Leu Val Met Phe Ile<br>1670 | tac tcc atc ttt ggc<br>Tyr Ser Ile Phe Gly<br>1675 | | 5175 |
| atg gcc aac ttc gct<br>Met Ala Asn Phe Ala<br>1680 | tat gtc aag tgg gag<br>Tyr Val Lys Trp Glu<br>1685 | gct ggc atc gac gac<br>Ala Gly Ile Asp Asp<br>1690 | | 5220 |
| atg ttc aac ttc cag<br>Met Phe Asn Phe Gln<br>1695 | acc ttc gcc aac agc<br>Thr Phe Ala Asn Ser<br>1700 | atg ctg tgc ctc ttc<br>Met Leu Cys Leu Phe<br>1705 | | 5265 |
| cag atc acc acg tcg<br>Gln Ile Thr Thr Ser<br>1710 | gcc ggc tgg gat ggc<br>Ala Gly Trp Asp Gly<br>1715 | ctc ctc agc ccc atc<br>Leu Leu Ser Pro Ile<br>1720 | | 5310 |
| ctc aac act ggg ccg<br>Leu Asn Thr Gly Pro<br>1725 | ccc tac tgc gac ccc<br>Pro Tyr Cys Asp Pro<br>1730 | act ctg ccc aac agc<br>Thr Leu Pro Asn Ser<br>1735 | | 5355 |
| aat ggc tct cgg ggg<br>Asn Gly Ser Arg Gly<br>1740 | gac tgc ggg agc cca<br>Asp Cys Gly Ser Pro<br>1745 | gcc gtg ggc atc ctc<br>Ala Val Gly Ile Leu<br>1750 | | 5400 |

```
                                                        -continued ttc ttc acc acc tac atc atc atc tcc ttc ctc atc gtg gtc aac        5445
Phe Phe Thr Thr Tyr Ile Ile Ile Ser Phe Leu Ile Val Val Asn
                    1755                1760                1765 atg tac att gcc atc atc ctg gag aac ttc agc gtg gcc acg gag        5490
Met Tyr Ile Ala Ile Ile Leu Glu Asn Phe Ser Val Ala Thr Glu
            1770                1775                1780 gag agc acc gag ccc ctg agt gag gac gac ttc gat atg ttc tat        5535
Glu Ser Thr Glu Pro Leu Ser Glu Asp Asp Phe Asp Met Phe Tyr
        1785                1790                1795 gag atc tgg gag aaa ttt gac cca gag gcc act cag ttt att gag        5580
Glu Ile Trp Glu Lys Phe Asp Pro Glu Ala Thr Gln Phe Ile Glu
    1800                1805                1810 tat tcg gtc ctg tct gac ttt gcc gac gcc ctg tct gag cca ctc        5625
Tyr Ser Val Leu Ser Asp Phe Ala Asp Ala Leu Ser Glu Pro Leu
1815                1820                1825 cgt atc gcc aag ccc aac cag ata agc ctc atc aac atg gac ctg        5670
Arg Ile Ala Lys Pro Asn Gln Ile Ser Leu Ile Asn Met Asp Leu
                    1830                1835                1840 ccc atg gtg agt ggg gac cgc atc cat tgc atg gac att ctc ttt        5715
Pro Met Val Ser Gly Asp Arg Ile His Cys Met Asp Ile Leu Phe
            1845                1850                1855 gcc ttc acc aaa agg gtc ctg ggg gag tct ggg gag atg gac gcc        5760
Ala Phe Thr Lys Arg Val Leu Gly Glu Ser Gly Glu Met Asp Ala
        1860                1865                1870 ctg aag atc cag atg gag gag aag ttc atg gca gcc aac cca tcc        5805
Leu Lys Ile Gln Met Glu Glu Lys Phe Met Ala Ala Asn Pro Ser
    1875                1880                1885 aag atc tcc tac gag ccc atc acc acc aca ctc cgg cgc aag cac        5850
Lys Ile Ser Tyr Glu Pro Ile Thr Thr Thr Leu Arg Arg Lys His
1890                1895                1900 gaa gag gtg tcg gcc atg gtt atc cag aga gcc ttc cgc agg cac        5895
Glu Glu Val Ser Ala Met Val Ile Gln Arg Ala Phe Arg Arg His
                    1905                1910                1915 ctg ctg caa cgc tct ttg aag cat gcc tcc ttc ctc ttc cgt cag        5940
Leu Leu Gln Arg Ser Leu Lys His Ala Ser Phe Leu Phe Arg Gln
            1920                1925                1930 cag gcg ggc agc ggc ctc tcc gaa gag gat gcc cct gag cga gag        5985
Gln Ala Gly Ser Gly Leu Ser Glu Glu Asp Ala Pro Glu Arg Glu
        1935                1940                1945 ggc ctc atc gcc tac gtg atg agt gag aac ttc tcc cga ccc ctt        6030
Gly Leu Ile Ala Tyr Val Met Ser Glu Asn Phe Ser Arg Pro Leu
    1950                1955                1960 ggc cca ccc tcc agc tcc tcc atc tcc tcc act tcc ttc cca ccc        6075
Gly Pro Pro Ser Ser Ser Ser Ile Ser Ser Thr Ser Phe Pro Pro
1965                1970                1975 tcc tat gac agt gtc act aga gcc acc agc gat aac ctc cag gtg        6120
Ser Tyr Asp Ser Val Thr Arg Ala Thr Ser Asp Asn Leu Gln Val
                    1980                1985                1990 cgg ggg tct gac tac agc cac agt gaa gat ctc gcc gac ttc ccc        6165
Arg Gly Ser Asp Tyr Ser His Ser Glu Asp Leu Ala Asp Phe Pro
            1995                2000                2005 cct tct ccg gac agg gac cgt gag tcc atc gtg tgagcctcgg             6208
Pro Ser Pro Asp Arg Asp Arg Glu Ser Ile Val
        2010                2015 cctggctggc caggacacac tgaaaagcag ccttttttcac catggcaaac ctaaatgcag  6268
tcagtcacaa accagcctgg ggccttcctg gctttgggag taagaaatgg gcctcggccc   6328
cgcggatcaa ccaggcagag ttctgtggcg ccgcgtggac agccggagca gttggcctgt   6388
```

```
gcttggaggc ctcagataga cctgtgacct ggtctggtca ggcaatgccc ctgcggctct   6448
ggaaagcaac ttcatcccag ctgctgaggc gaaatataaa actgagactg tatatgttgt   6508
gaatgggctt tcataaattt attatatttg atattttttt acttgagcaa agaactaagg   6568 attttccat ggacatgggc agcaattcac gctgtctctt cttaaccctg aacaagagtg    6628
tctatggagc agccggaagt ctgttctcaa agcagaagtg gaatccagtg tggctcccac   6688
aggtcttcac tgcccagggg tcgaatgggg tcccctccc acttgacctg agatgctggg    6748
agggctgaac ccccactcac acaagcacac acacacacag tcctcacaca cggaggccag   6808
acacaggccg tgggacccag gctcccagcc taagggagac aggcctttcc ctgccggccc   6868
cccaaggatg gggttcttgt ccacggggct cactctggcc ccctattgtc tcccaaggtc   6928 ccatttccc ccttgtgttt tcacgcaggt catattgtca gtcctacaaa aataaaaggc    6988
ttccagagga gagtggcctg ggtcccagg gctgggccnt aggcactgat agttgccttt    7048
tcttcccctc ctgtaagagt attaacaaaa ccaaaggaca caaggtgca agccccattc    7108 acggcctggc atgcagcttg tccttgctcc tggaacctgg caggccctgc agccagcca    7168 atggaagaga ggggctgagc catgggggtt tggggctaag aagttcacca gccctgagcc   7228
atggsnsccc tcagcctgcc tgaagagagg aaactggcga tctcccaggg ctctctggac   7288
catacncgga ggagttttcn ngtgtggtct ccagctcctc tccagacaca gagacatggg   7348
agtggggagc ggacgttggc cctggccctg tgcagggaaa gggatggtca ggcccagttc   7408
tcgtgcccct tagaggggaa tgaaccatgg caccttgag agaggggca ctgtggtcag    7468 gcccagcctc tctggcnnag tcccgggatc ctgatggcac ccacacagag gacctctttg   7528
gggcaagatc caggtgggntc ccataggtct tgtgaaaagg cttttcagg gaaaaatatt   7588 ttactagtcc aatcacccc aggacctctt cagctgctga caatcctatt tagcatatgc    7648
aaatctttta acatagagaa ctgtcaccct gaggtaacag ggtcaactgg cgaagagcag   7708 gccaggggc ttggctgnnc cattccagct ctnccacnga nnnnctccwm ncnnnnncat    7768
nnctcccagg ccacctcagt ctcanctgcc ggctctgggc tggctnctcc taacctacct   7828
nnccgagctg tcggagggct ggacatttgt ggcagtgctg aanggggcat tgsnggcgag   7888
taaagtatta kgtttcttct tgtcacccca gttcccttgg tggcaacccc agacccaacc   7948
catgcccctg acagatctag ttctcttcts ctgtgttccc tttgagtccn gtgtgggaca   8008
cggtttaact gtcccagcga gatttctcca agtngaaatc ctattttgt agatctccat    8068 gctttgnctc tcaaggcttg gagaggtatg tgcccctcct nggbnctcac cgcctgctac   8128
acaggcagga atgcggnttg ggaggcaggt cgggctssna gcccagctgg ccggaaggag   8188
actgtggttt ttgtgtgtgt ggacagcncg ggagctttga dacaggntgc ctggggctgg   8248
ctgcagacgg tgtggttggg ggtgggaggt gagctagacc nnnccccttag cttttagcct   8308 ggctgtcacc ttttttaattt ccagaactgc acaatgacca gnaggagggg agaagagagt   8368
aggaaaaagg agggaaggac agacatcaag tgccagatgt tgtctgaact aatcgagcac   8428
ttctcaccaa acttcnngta taaataaaat acatannnng gggcaaacca ataaatggct   8488
tac                                                                 8491
```

<210> SEQ ID NO 2
<211> LENGTH: 2016
<212> TYPE: PRT
<213> ORGANISM: Homo sapiens
<220> FEATURE:
<221> NAME/KEY: misc_feature
<222> LOCATION: (1)..(8491)
<223> OTHER INFORMATION: n may be any base

<400> SEQUENCE: 2

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Val Arg Arg Ala Val Lys Ile Leu
        115                 120                 125

Val His Ser Leu Phe Asn Met Leu Ile Met Cys Thr Ile Leu Thr Asn
130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Ala Phe Cys Leu His Ala Phe Thr Phe Leu Arg Asp Pro
            180                 185                 190

Trp Asn Trp Leu Asp Phe Ser Val Ile Ile Met Ala Tyr Thr Thr Glu
        195                 200                 205

Phe Val Asp Leu Gly Asn Val Ser Ala Leu Arg Thr Phe Arg Val Leu
210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
370                 375                 380

Ala Gly Lys Ile Tyr Met Ile Phe Phe Met Leu Val Ile Phe Leu Gly
385                 390                 395                 400
```

```
Ser Phe Tyr Leu Val Asn Leu Ile Leu Ala Val Val Ala Met Ala Tyr
            405                 410                 415
Glu Glu Gln Asn Gln Ala Thr Ile Ala Glu Thr Glu Lys Glu Lys
        420                 425                 430
Arg Phe Gln Glu Ala Met Glu Met Leu Lys Lys Glu His Glu Ala Leu
        435                 440                 445
Thr Ile Arg Gly Val Asp Thr Val Ser Arg Ser Ser Leu Glu Met Ser
    450                 455                 460
Pro Leu Ala Pro Val Asn Ser His Glu Arg Arg Ser Lys Arg Lys
465             470                 475                 480
Arg Met Ser Ser Gly Thr Glu Glu Cys Gly Glu Asp Arg Leu Pro Lys
            485                 490                 495
Ser Asp Ser Glu Asp Gly Pro Arg Ala Met Asn His Leu Ser Leu Thr
            500                 505                 510
Arg Gly Leu Ser Arg Thr Ser Met Lys Pro Arg Ser Ser Arg Gly Ser
            515                 520                 525
Ile Phe Thr Phe Arg Arg Arg Asp Leu Gly Ser Glu Ala Asp Phe Ala
    530                 535                 540
Asp Asp Glu Asn Ser Thr Ala Arg Glu Ser Glu Ser His His Thr Ser
545                 550                 555                 560
Leu Leu Val Pro Trp Pro Leu Arg Arg Thr Ser Ala Gln Gly Gln Pro
                565                 570                 575
Ser Pro Gly Thr Ser Ala Pro Gly His Ala Leu His Gly Lys Lys Asn
            580                 585                 590
Ser Thr Val Asp Cys Asn Gly Val Val Ser Leu Leu Gly Ala Gly Asp
            595                 600                 605
Pro Glu Ala Thr Ser Pro Gly Ser His Leu Leu Arg Pro Val Met Leu
            610                 615                 620
Glu His Pro Pro Asp Thr Thr Pro Ser Glu Glu Pro Gly Gly Pro
625                 630                 635                 640
Gln Met Leu Thr Ser Gln Ala Pro Cys Val Asp Gly Phe Glu Glu Pro
                645                 650                 655
Gly Ala Arg Gln Arg Ala Leu Ser Ala Val Ser Val Leu Thr Ser Ala
            660                 665                 670
Leu Glu Glu Leu Glu Glu Ser Arg His Lys Cys Pro Pro Cys Trp Asn
            675                 680                 685
Arg Leu Ala Gln Arg Tyr Leu Ile Trp Glu Cys Cys Pro Leu Trp Met
    690                 695                 700
Ser Ile Lys Gln Gly Val Lys Leu Val Val Met Asp Pro Phe Thr Asp
705                 710                 715                 720
Leu Thr Ile Thr Met Cys Ile Val Leu Asn Thr Leu Phe Met Ala Leu
                725                 730                 735
Glu His Tyr Asn Met Thr Ser Glu Phe Glu Glu Met Leu Gln Val Gly
                740                 745                 750
Asn Leu Val Phe Thr Gly Ile Phe Thr Ala Glu Met Thr Phe Lys Ile
            755                 760                 765
Ile Ala Leu Asp Pro Tyr Tyr Tyr Phe Gln Gln Gly Trp Asn Ile Phe
    770                 775                 780
Asp Ser Ile Ile Val Ile Leu Ser Leu Met Glu Leu Gly Leu Ser Arg
785                 790                 795                 800
Met Ser Asn Leu Ser Val Leu Arg Ser Phe Arg Leu Leu Arg Val Phe
                805                 810                 815
```

-continued

Lys Leu Ala Lys Ser Trp Pro Thr Leu Asn Thr Leu Ile Lys Ile Ile
        820                 825                 830

Gly Asn Ser Val Gly Ala Leu Gly Asn Leu Thr Leu Val Leu Ala Ile
        835                 840                 845

Ile Val Phe Ile Phe Ala Val Val Gly Met Gln Leu Phe Gly Lys Asn
        850                 855                 860

Tyr Ser Glu Leu Arg Asp Ser Asp Ser Gly Leu Leu Pro Arg Trp His
865                 870                 875                 880

Met Met Asp Phe Phe His Ala Phe Leu Ile Ile Phe Arg Ile Leu Cys
                885                 890                 895

Gly Glu Trp Ile Glu Thr Met Trp Asp Cys Met Glu Val Ser Gly Gln
        900                 905                 910

Ser Leu Cys Leu Leu Val Phe Leu Leu Val Met Val Ile Gly Asn Leu
        915                 920                 925

Val Val Leu Asn Leu Phe Leu Ala Leu Leu Ser Ser Phe Ser Ala
        930                 935                 940

Asp Asn Leu Thr Ala Pro Asp Glu Asp Arg Glu Met Asn Asn Leu Gln
945                 950                 955                 960

Leu Ala Leu Ala Arg Ile Gln Arg Gly Leu Arg Phe Val Lys Arg Thr
                965                 970                 975

Thr Trp Asp Phe Cys Cys Gly Leu Leu Arg His Arg Pro Gln Lys Pro
            980                 985                 990

Ala Ala Leu Ala Ala Gln Gly Gln Leu Pro Ser Cys Ile Ala Thr Pro
            995                 1000                1005

Tyr Ser Pro Pro Pro Glu Thr Glu Lys Val Pro Pro Thr Arg
    1010                1015                1020

Lys Glu Thr Gln Phe Glu Gly Glu Gln Pro Gly Gln Gly Thr
    1025                1030                1035

Pro Gly Asp Pro Glu Pro Val Cys Val Pro Ile Ala Val Ala Glu
    1040                1045                1050

Ser Asp Thr Asp Asp Gln Glu Glu Asp Glu Glu Asn Ser Leu Gly
    1055                1060                1065

Thr Glu Glu Glu Ser Ser Lys Gln Gln Glu Ser Gln Pro Val Ser
    1070                1075                1080

Gly Trp Pro Arg Gly Pro Pro Asp Ser Arg Thr Trp Ser Gln Val
    1085                1090                1095

Ser Ala Thr Ala Ser Ser Glu Ala Glu Ala Ser Ala Ser Gln Ala
    1100                1105                1110

Asp Trp Arg Gln Gln Trp Lys Ala Glu Pro Gln Ala Pro Gly Cys
    1115                1120                1125

Gly Glu Thr Pro Glu Asp Ser Cys Ser Glu Gly Ser Thr Ala Asp
    1130                1135                1140

Met Thr Asn Thr Ala Glu Leu Leu Glu Gln Ile Pro Asp Leu Gly
    1145                1150                1155

Gln Asp Val Lys Asp Pro Glu Asp Cys Phe Thr Glu Gly Cys Val
    1160                1165                1170

Arg Arg Cys Pro Cys Cys Ala Val Asp Thr Thr Gln Ala Pro Gly
    1175                1180                1185

Lys Val Trp Trp Arg Leu Arg Lys Thr Cys Tyr His Ile Val Glu
    1190                1195                1200

His Ser Trp Phe Glu Thr Phe Ile Ile Phe Met Ile Leu Leu Ser
    1205                1210                1215

Ser Gly Ala Leu Ala Phe Glu Asp Ile Tyr Leu Glu Glu Arg Lys

-continued

```
            1220                1225                1230
Thr Ile Lys Val Leu Leu Glu Tyr Ala Asp Lys Met Phe Thr Tyr
    1235                1240                1245
Val Phe Val Leu Glu Met Leu Leu Lys Trp Val Ala Tyr Gly Phe
    1250                1255                1260
Lys Lys Tyr Phe Thr Asn Ala Trp Cys Trp Leu Asp Phe Leu Ile
    1265                1270                1275
Val Asp Val Ser Leu Val Ser Leu Val Ala Asn Thr Leu Gly Phe
    1280                1285                1290
Ala Glu Met Gly Pro Ile Lys Ser Leu Arg Thr Leu Arg Ala Leu
    1295                1300                1305
Arg Pro Leu Arg Ala Leu Ser Arg Phe Glu Gly Met Arg Val Val
    1310                1315                1320
Val Asn Ala Leu Val Gly Ala Ile Pro Ser Ile Met Asn Val Leu
    1325                1330                1335
Leu Val Cys Leu Ile Phe Trp Leu Ile Phe Ser Ile Met Gly Val
    1340                1345                1350
Asn Leu Phe Ala Gly Lys Phe Gly Arg Cys Ile Asn Gln Thr Glu
    1355                1360                1365
Gly Asp Leu Pro Leu Asn Tyr Thr Ile Val Asn Asn Lys Ser Gln
    1370                1375                1380
Cys Glu Ser Leu Asn Leu Thr Gly Glu Leu Tyr Trp Thr Lys Val
    1385                1390                1395
Lys Val Asn Phe Asp Asn Val Gly Ala Gly Tyr Leu Ala Leu Leu
    1400                1405                1410
Gln Val Ala Thr Phe Lys Gly Trp Met Asp Ile Met Tyr Ala Ala
    1415                1420                1425
Val Asp Ser Arg Gly Tyr Glu Glu Gln Pro Gln Trp Glu Tyr Asn
    1430                1435                1440
Leu Tyr Met Tyr Ile Tyr Phe Val Ile Phe Ile Ile Phe Gly Ser
    1445                1450                1455
Phe Phe Thr Leu Asn Leu Phe Ile Gly Val Ile Ile Asp Asn Phe
    1460                1465                1470
Asn Gln Gln Lys Lys Lys Leu Gly Gly Gln Asp Ile Phe Met Thr
    1475                1480                1485
Glu Glu Gln Lys Lys Tyr Tyr Asn Ala Met Lys Lys Leu Gly Ser
    1490                1495                1500
Lys Lys Pro Gln Lys Pro Ile Pro Arg Pro Leu Asn Lys Tyr Gln
    1505                1510                1515
Gly Phe Ile Phe Asp Ile Val Thr Lys Gln Ala Phe Asp Val Thr
    1520                1525                1530
Ile Met Phe Leu Ile Cys Leu Asn Met Val Thr Met Met Val Glu
    1535                1540                1545
Thr Asp Asp Gln Ser Pro Glu Lys Ile Asn Ile Leu Ala Lys Ile
    1550                1555                1560
Asn Leu Leu Phe Val Ala Ile Phe Thr Gly Glu Cys Ile Val Lys
    1565                1570                1575
Leu Ala Ala Leu Arg His Tyr Tyr Phe Thr Asn Ser Trp Asn Ile
    1580                1585                1590
Phe Asp Phe Val Val Val Ile Leu Ser Ile Val Gly Thr Val Leu
    1595                1600                1605
Ser Asp Ile Ile Gln Lys Tyr Phe Phe Ser Pro Thr Leu Phe Arg
    1610                1615                1620
```

```
Val Ile Arg Leu Ala Arg Ile Gly Arg Ile Leu Arg Leu Ile Arg
1625                1630                1635

Gly Ala Lys Gly Ile Arg Thr Leu Leu Phe Ala Leu Met Met Ser
1640                1645                1650

Leu Pro Ala Leu Phe Asn Ile Gly Leu Leu Leu Phe Leu Val Met
1655                1660                1665

Phe Ile Tyr Ser Ile Phe Gly Met Ala Asn Phe Ala Tyr Val Lys
1670                1675                1680

Trp Glu Ala Gly Ile Asp Asp Met Phe Asn Phe Gln Thr Phe Ala
1685                1690                1695

Asn Ser Met Leu Cys Leu Phe Gln Ile Thr Thr Ser Ala Gly Trp
1700                1705                1710

Asp Gly Leu Leu Ser Pro Ile Leu Asn Thr Gly Pro Pro Tyr Cys
1715                1720                1725

Asp Pro Thr Leu Pro Asn Ser Asn Gly Ser Arg Gly Asp Cys Gly
1730                1735                1740

Ser Pro Ala Val Gly Ile Leu Phe Phe Thr Thr Tyr Ile Ile Ile
1745                1750                1755

Ser Phe Leu Ile Val Val Asn Met Tyr Ile Ala Ile Ile Leu Glu
1760                1765                1770

Asn Phe Ser Val Ala Thr Glu Glu Ser Thr Glu Pro Leu Ser Glu
1775                1780                1785

Asp Asp Phe Asp Met Phe Tyr Glu Ile Trp Glu Lys Phe Asp Pro
1790                1795                1800

Glu Ala Thr Gln Phe Ile Glu Tyr Ser Val Leu Ser Asp Phe Ala
1805                1810                1815

Asp Ala Leu Ser Glu Pro Leu Arg Ile Ala Lys Pro Asn Gln Ile
1820                1825                1830

Ser Leu Ile Asn Met Asp Leu Pro Met Val Ser Gly Asp Arg Ile
1835                1840                1845

His Cys Met Asp Ile Leu Phe Ala Phe Thr Lys Arg Val Leu Gly
1850                1855                1860

Glu Ser Gly Glu Met Asp Ala Leu Lys Ile Gln Met Glu Glu Lys
1865                1870                1875

Phe Met Ala Ala Asn Pro Ser Lys Ile Ser Tyr Glu Pro Ile Thr
1880                1885                1890

Thr Thr Leu Arg Arg Lys His Glu Glu Val Ser Ala Met Val Ile
1895                1900                1905

Gln Arg Ala Phe Arg Arg His Leu Leu Gln Arg Ser Leu Lys His
1910                1915                1920

Ala Ser Phe Leu Phe Arg Gln Gln Ala Gly Ser Gly Leu Ser Glu
1925                1930                1935

Glu Asp Ala Pro Glu Arg Glu Gly Leu Ile Ala Tyr Val Met Ser
1940                1945                1950

Glu Asn Phe Ser Arg Pro Leu Gly Pro Pro Ser Ser Ser Ser Ile
1955                1960                1965

Ser Ser Thr Ser Phe Pro Pro Ser Tyr Asp Ser Val Thr Arg Ala
1970                1975                1980

Thr Ser Asp Asn Leu Gln Val Arg Gly Ser Asp Tyr Ser His Ser
1985                1990                1995

Glu Asp Leu Ala Asp Phe Pro Pro Ser Pro Asp Arg Asp Arg Glu
2000                2005                2010
```

```
Ser Ile  Val
     2015

<210> SEQ ID NO 3
<211> LENGTH: 8491
<212> TYPE: DNA
<213> ORGANISM: Homo sapiens
<220> FEATURE:
<221> NAME/KEY: CDS
<222> LOCATION: (151)..(6198)
<220> FEATURE:
<221> NAME/KEY: misc_feature
<222> LOCATION: (1)..(8491)
<223> OTHER INFORMATION: n may be any base

<400> SEQUENCE: 3
gccgctgagc ctgcgcccag tgccccgagc cccgcgccga gccgagtccg cgccaagcag        60
cagccgccca ccccggggcc cggccggggg accagcagct tccccacagg caacgtgagg       120
agagcctgtg cccagaagca ggatgagaag atg gca aac ttc cta tta cct cgg       174
                                Met Ala Asn Phe Leu Leu Pro Arg
                                  1               5 ggc acc agc agc ttc cgc agg ttc aca cgg gag tcc ctg gca gcc atc        222
Gly Thr Ser Ser Phe Arg Arg Phe Thr Arg Glu Ser Leu Ala Ala Ile
     10                  15                  20 gag aag cgc atg gcg gag aag caa gcc cgc ggc tca acc acc ttg cag        270
Glu Lys Arg Met Ala Glu Lys Gln Ala Arg Gly Ser Thr Thr Leu Gln
 25                  30                  35                  40 gag agc cga gag ggg ctg ccc gag gag gag gct ccc cgg ccc cag ctg        318
Glu Ser Arg Glu Gly Leu Pro Glu Glu Glu Ala Pro Arg Pro Gln Leu
                 45                  50                  55 gac ctg cag gcc tcc aaa aag ctg cca gat ctc tat ggc aat cca ccc        366
Asp Leu Gln Ala Ser Lys Lys Leu Pro Asp Leu Tyr Gly Asn Pro Pro
             60                  65                  70 caa gag ctc atc gga gag ccc ctg gag gac ctg gac ccc ttc tat agc        414
Gln Glu Leu Ile Gly Glu Pro Leu Glu Asp Leu Asp Pro Phe Tyr Ser
         75                  80                  85 acc caa aag act ttc atc gta ctg aat aaa ggc aag acc atc ttc cgg        462
Thr Gln Lys Thr Phe Ile Val Leu Asn Lys Gly Lys Thr Ile Phe Arg
     90                  95                 100 ttc agt gcc acc aac gcc ttg tat gtc ctc agt ccc ttc cac cca gtt        510
Phe Ser Ala Thr Asn Ala Leu Tyr Val Leu Ser Pro Phe His Pro Val
105                 110                 115                 120 cgg aga gcg gct gtg aag att ctg gtt cac tcg ctc ttc aac atg ctc        558
Arg Arg Ala Ala Val Lys Ile Leu Val His Ser Leu Phe Asn Met Leu
                125                 130                 135 atc atg tgc acc atc ctc acc aac tgc gtg ttc atg gcc cag cac gac        606
Ile Met Cys Thr Ile Leu Thr Asn Cys Val Phe Met Ala Gln His Asp
            140                 145                 150 cct cca ccc tgg acc aag tat gtc gag tac acc ttc acc gcc att tac        654
Pro Pro Pro Trp Thr Lys Tyr Val Glu Tyr Thr Phe Thr Ala Ile Tyr
        155                 160                 165 acc ttt gag tct ctg gtc aag att ctg gct cga gct ttc tgc ctg cac        702
Thr Phe Glu Ser Leu Val Lys Ile Leu Ala Arg Ala Phe Cys Leu His
    170                 175                 180 gcg ttc act ttc ctt cgg gac cca tgg aac tgg ctg gac ttt agt gtg        750
Ala Phe Thr Phe Leu Arg Asp Pro Trp Asn Trp Leu Asp Phe Ser Val
185                 190                 195                 200 att atc atg gca tac aca act gaa ttt gtg gac ctg ggc aat gtc tca        798
Ile Ile Met Ala Tyr Thr Thr Glu Phe Val Asp Leu Gly Asn Val Ser
                205                 210                 215 gcc tta cgc acc ttc cga gtc ctc cgg gcc ctg aaa act ata tca gtc        846
```

```
Ala Leu Arg Thr Phe Arg Val Leu Arg Ala Leu Lys Thr Ile Ser Val
            220                 225                 230 att tca ggg ctg aag acc atc gtg ggg gcc ctg atc cag tct gtg aag      894
Ile Ser Gly Leu Lys Thr Ile Val Gly Ala Leu Ile Gln Ser Val Lys
        235                 240                 245 aag ctg gct gat gtg atg gtc ctc aca gtc ttc tgc ctc agc gtc ttt      942
Lys Leu Ala Asp Val Met Val Leu Thr Val Phe Cys Leu Ser Val Phe
250                 255                 260 gcc ctc atc ggc ctg cag ctc ttc atg ggc aac cta agg cac aag tgt      990
Ala Leu Ile Gly Leu Gln Leu Phe Met Gly Asn Leu Arg His Lys Cys
265                 270                 275                 280 gtg cgc aac ttc aca gcg ctc aac ggc acc aac ggc tcc gtg gag gcc     1038
Val Arg Asn Phe Thr Ala Leu Asn Gly Thr Asn Gly Ser Val Glu Ala
                285                 290                 295 gac ggc ttg gtc tgg gaa tcc ctg gac ctt tac ctc agt gat cca gaa     1086
Asp Gly Leu Val Trp Glu Ser Leu Asp Leu Tyr Leu Ser Asp Pro Glu
            300                 305                 310 aat tac ctg ctc aag aac ggc acc tct gat gtg tta ctg tgt ggg aac     1134
Asn Tyr Leu Leu Lys Asn Gly Thr Ser Asp Val Leu Leu Cys Gly Asn
        315                 320                 325 agc tct gac gct ggg aca tgt ccg gag ggc tac cgg tgc cta aag gca     1182
Ser Ser Asp Ala Gly Thr Cys Pro Glu Gly Tyr Arg Cys Leu Lys Ala
330                 335                 340 ggc gag aac ccc gac cac ggc tac acc agc ttc gat tcc ttt gcc tgg     1230
Gly Glu Asn Pro Asp His Gly Tyr Thr Ser Phe Asp Ser Phe Ala Trp
345                 350                 355                 360 gcc ttt ctt gca ctc ttc cgc ctg atg acg cag gac tgc tgg gag cgc     1278
Ala Phe Leu Ala Leu Phe Arg Leu Met Thr Gln Asp Cys Trp Glu Arg
                365                 370                 375 ctc tat cag cag acc ctc agg tcc gca ggg aag atc tac atg atc ttc     1326
Leu Tyr Gln Gln Thr Leu Arg Ser Ala Gly Lys Ile Tyr Met Ile Phe
            380                 385                 390 ttc atg ctt gtc atc ttc ctg ggg tcc ttc tac ctg gtg aac ctg atc     1374
Phe Met Leu Val Ile Phe Leu Gly Ser Phe Tyr Leu Val Asn Leu Ile
        395                 400                 405 ctg gcc gtg gtc gca atg gcc tat gag gag caa aac caa gcc acc atc     1422
Leu Ala Val Val Ala Met Ala Tyr Glu Glu Gln Asn Gln Ala Thr Ile
410                 415                 420 gct gag acc gag gag aag gaa aag cgc ttc cag gag gcc atg gaa atg     1470
Ala Glu Thr Glu Glu Lys Glu Lys Arg Phe Gln Glu Ala Met Glu Met
425                 430                 435                 440 ctc aag aaa gaa cac gag gcc ctc acc atc agg ggt gtg gat acc gtg     1518
Leu Lys Lys Glu His Glu Ala Leu Thr Ile Arg Gly Val Asp Thr Val
                445                 450                 455 tcc cgt agc tcc ttg gag atg tcc cct ttg gcc cca gta aac agc cat     1566
Ser Arg Ser Ser Leu Glu Met Ser Pro Leu Ala Pro Val Asn Ser His
            460                 465                 470 gag aga aga agc aag agg aga aaa cgg atg tct tca gga act gag gag     1614
Glu Arg Arg Ser Lys Arg Arg Lys Arg Met Ser Ser Gly Thr Glu Glu
        475                 480                 485 tgt ggg gag gac agg ctc ccc aag tct gac tca gaa gat ggt ccc aga     1662
Cys Gly Glu Asp Arg Leu Pro Lys Ser Asp Ser Glu Asp Gly Pro Arg
490                 495                 500 gca atg aat cat ctc agc ctc acc cgt ggc ctc agc agg act tct atg     1710
Ala Met Asn His Leu Ser Leu Thr Arg Gly Leu Ser Arg Thr Ser Met
505                 510                 515                 520 aag cca cgt tcc agc cgc ggg agc att ttc acc ttt cgc agg cga gac     1758
Lys Pro Arg Ser Ser Arg Gly Ser Ile Phe Thr Phe Arg Arg Arg Asp
                525                 530                 535
```

```
ctg ggt tct gaa gca gat ttt gca gat gat gaa aac agc aca gcg cgg         1806
Leu Gly Ser Glu Ala Asp Phe Ala Asp Asp Glu Asn Ser Thr Ala Arg
            540                 545                 550 gag agc gag agc cac cac aca tca ctg ctg gtg ccc tgg ccc ctg cgc         1854
Glu Ser Glu Ser His His Thr Ser Leu Leu Val Pro Trp Pro Leu Arg
555                 560                 565 cgg acc agt gcc cag gga cag ccc agt ccc gga acc tcg gct cct ggc         1902
Arg Thr Ser Ala Gln Gly Gln Pro Ser Pro Gly Thr Ser Ala Pro Gly
    570                 575                 580 cac gcc ctc cat ggc aaa aag aac agc act gtg gac tgc aat ggg gtg         1950
His Ala Leu His Gly Lys Lys Asn Ser Thr Val Asp Cys Asn Gly Val
585                 590                 595                 600 gtc tca tta ctg ggg gca ggc gac cca gag gcc aca tcc cca gga agc         1998
Val Ser Leu Leu Gly Ala Gly Asp Pro Glu Ala Thr Ser Pro Gly Ser
            605                 610                 615 cac ctc ctc cgc cct gtg atg cta gag cac ccg cca gac acg acc acg         2046
His Leu Leu Arg Pro Val Met Leu Glu His Pro Pro Asp Thr Thr Thr
        620                 625                 630 cca tcg gag gag cca ggc ggc ccc cag atg ctg acc tcc cag gct ccg         2094
Pro Ser Glu Glu Pro Gly Gly Pro Gln Met Leu Thr Ser Gln Ala Pro
635                 640                 645 tgt gta gat ggc ttc gag gag cca gga gca cgg cag cgg gcc ctc agc         2142
Cys Val Asp Gly Phe Glu Glu Pro Gly Ala Arg Gln Arg Ala Leu Ser
    650                 655                 660 gca gtc agc gtc ctc aca agc gca ctg gaa gag tta gag gag tct cgc         2190
Ala Val Ser Val Leu Thr Ser Ala Leu Glu Glu Leu Glu Glu Ser Arg
665                 670                 675                 680 cac aag tgt cca cca tgc tgg aac cgt ctc gcc cag cgc tac ctg atc         2238
His Lys Cys Pro Pro Cys Trp Asn Arg Leu Ala Gln Arg Tyr Leu Ile
            685                 690                 695 tgg gag tgc tgc ccg ctg tgg atg tcc atc aag cag gga gtg aag ttg         2286
Trp Glu Cys Cys Pro Leu Trp Met Ser Ile Lys Gln Gly Val Lys Leu
        700                 705                 710 gtg gtc atg gac ccg ttt act gac ctc acc atc act atg tgc atc gta         2334
Val Val Met Asp Pro Phe Thr Asp Leu Thr Ile Thr Met Cys Ile Val
        715                 720                 725 ctc aac aca ctc ttc atg gcg ctg gag cac tac aac atg aca agt gaa         2382
Leu Asn Thr Leu Phe Met Ala Leu Glu His Tyr Asn Met Thr Ser Glu
730                 735                 740 ttc gag gag atg ctg cag gtc gga aac ctg gtc ttc aca ggg att ttc         2430
Phe Glu Glu Met Leu Gln Val Gly Asn Leu Val Phe Thr Gly Ile Phe
745                 750                 755                 760 aca gca gag atg acc ttc aag atc att gcc ctc gac ccc tac tac tac         2478
Thr Ala Glu Met Thr Phe Lys Ile Ile Ala Leu Asp Pro Tyr Tyr Tyr
            765                 770                 775 ttc caa cag ggc tgg aac atc ttc gac agc atc atc gtc atc ctt agc         2526
Phe Gln Gln Gly Trp Asn Ile Phe Asp Ser Ile Ile Val Ile Leu Ser
        780                 785                 790 ctc atg gag ctg ggc ctg tcc cgc atg agc aac ttg tcg gtg ctg cgc         2574
Leu Met Glu Leu Gly Leu Ser Arg Met Ser Asn Leu Ser Val Leu Arg
        795                 800                 805 tcc ttc cgc ctg ctg cgg gtc ttc aag ctg gcc aaa tca tgg ccc acc         2622
Ser Phe Arg Leu Leu Arg Val Phe Lys Leu Ala Lys Ser Trp Pro Thr
810                 815                 820 ctg aac aca ctc atc aag atc atc ggg aac tca gtg ggg gca ctg ggg         2670
Leu Asn Thr Leu Ile Lys Ile Ile Gly Asn Ser Val Gly Ala Leu Gly
825                 830                 835                 840 aac ctg aca ctg gtg cta gcc atc atc gtg ttc atc ttt gct gtg gtg         2718
Asn Leu Thr Leu Val Leu Ala Ile Ile Val Phe Ile Phe Ala Val Val
            845                 850                 855
```

-continued

| | |
|---|---|
| ggc atg cag ctc ttt ggc aag aac tac tcg gag ctg agg gac agc gac<br>Gly Met Gln Leu Phe Gly Lys Asn Tyr Ser Glu Leu Arg Asp Ser Asp<br>860                     865                     870 | 2766 |
| tca ggc ctg ctg cct cgc tgg cac atg atg gac ttc ttt cat gcc ttc<br>Ser Gly Leu Leu Pro Arg Trp His Met Met Asp Phe Phe His Ala Phe<br>875                     880                     885 | 2814 |
| cta atc atc ttc cgc atc ctc tgt gga gag tgg atc gag acc atg tgg<br>Leu Ile Ile Phe Arg Ile Leu Cys Gly Glu Trp Ile Glu Thr Met Trp<br>890                     895                     900 | 2862 |
| gac tgc atg gag gtg tcg ggg cag tca tta tgc ctg ctg gtc ttc ttg<br>Asp Cys Met Glu Val Ser Gly Gln Ser Leu Cys Leu Leu Val Phe Leu<br>905                     910                     915                     920 | 2910 |
| ctt gtt atg gtc att ggc aac ctt gtg gtc ctg aat ctc ttc ctg gcc<br>Leu Val Met Val Ile Gly Asn Leu Val Val Leu Asn Leu Phe Leu Ala<br>925                     930                     935 | 2958 |
| ttg ctc agc tcc ttc agt gca gac aac ctc aca gcc cct gat gag<br>Leu Leu Leu Ser Ser Phe Ser Ala Asp Asn Leu Thr Ala Pro Asp Glu<br>940                     945                     950 | 3006 |
| gac aga gag atg aac aac ctc cag ctg gcc ctg gcc cgc atc cag agg<br>Asp Arg Glu Met Asn Asn Leu Gln Leu Ala Leu Ala Arg Ile Gln Arg<br>955                     960                     965 | 3054 |
| ggc ctg cgc ttt gtc aag cgg acc acc tgg gat ttc tgc tgt ggt ctc<br>Gly Leu Arg Phe Val Lys Arg Thr Thr Trp Asp Phe Cys Cys Gly Leu<br>970                     975                     980 | 3102 |
| ctg cgg cac cgg cct cag aag ccc gca gcc ctt gcc gcc cag ggc cag<br>Leu Arg His Arg Pro Gln Lys Pro Ala Ala Leu Ala Ala Gln Gly Gln<br>985                     990                     995                   1000 | 3150 |
| ctg ccc agc tgc att gcc acc ccc tac tcc ccg cca ccc cca gag<br>Leu Pro Ser Cys Ile Ala Thr Pro Tyr Ser Pro Pro Pro Pro Glu<br>1005                    1010                  1015 | 3195 |
| acg gag aag gtg cct ccc acc cgc aag gaa aca cag ttt gag gaa<br>Thr Glu Lys Val Pro Pro Thr Arg Lys Glu Thr Gln Phe Glu Glu<br>1020                  1025                 1030 | 3240 |
| ggc gag caa cca ggc cag ggc acc ccc ggg gat cca gag ccc gtg<br>Gly Glu Gln Pro Gly Gln Gly Thr Pro Gly Asp Pro Glu Pro Val<br>1035                  1040                 1045 | 3285 |
| tgt gtg ccc atc gct gtg gcc gag tca gac aca gat gac caa gaa<br>Cys Val Pro Ile Ala Val Ala Glu Ser Asp Thr Asp Asp Gln Glu<br>1050                  1055                 1060 | 3330 |
| gag gat gag gag aac agc ctg ggc acg gag gag gag tcc agc aag<br>Glu Asp Glu Glu Asn Ser Leu Gly Thr Glu Glu Glu Ser Ser Lys<br>1065                  1070                 1075 | 3375 |
| cag cag gaa tcc cag cct gtg tcc ggc tgg ccc aga ggc cct ccg<br>Gln Gln Glu Ser Gln Pro Val Ser Gly Trp Pro Arg Gly Pro Pro<br>1080                  1085                 1090 | 3420 |
| gat tcc agg acc tgg agc cag gtg tca gcg act gcc tac tct gag<br>Asp Ser Arg Thr Trp Ser Gln Val Ser Ala Thr Ala Tyr Ser Glu<br>1095                  1100                 1105 | 3465 |
| gcc gag gcc agt gca tct cag gcc gac tgg cgg cag cag tgg aaa<br>Ala Glu Ala Ser Ala Ser Gln Ala Asp Trp Arg Gln Gln Trp Lys<br>1110                  1115                 1120 | 3510 |
| gcg gaa ccc cag gcc cca ggg tgc ggt gag acc cca gag gac agt<br>Ala Glu Pro Gln Ala Pro Gly Cys Gly Glu Thr Pro Glu Asp Ser<br>1125                  1130                 1135 | 3555 |
| tgc tcc gag ggc agc aca gca gac atg acc aac acc gct gag ctc<br>Cys Ser Glu Gly Ser Thr Ala Asp Met Thr Asn Thr Ala Glu Leu<br>1140                  1145                 1150 | 3600 |
| ctg gag cag atc cct gac ctc ggc cag gat gtc aag gac cca gag<br>Leu Glu Gln Ile Pro Asp Leu Gly Gln Asp Val Lys Asp Pro Glu | 3645 |

```
                        1155                1160                1165
gac tgc ttc act gaa  ggc tgt gtc cgg cgc  tgt ccc tgc tgt gcg       3690
Asp Cys Phe Thr Glu  Gly Cys Val Arg Arg  Cys Pro Cys Cys Ala
                1170                1175                1180 gtg gac acc aca cag  gcc cca ggg aag gtc  tgg tgg cgg ttg cgc       3735
Val Asp Thr Thr Gln  Ala Pro Gly Lys Val  Trp Trp Arg Leu Arg
                1185                1190                1195 aag acc tgc tac cac  atc gtg gag cac agc  tgg ttc gag aca ttc       3780
Lys Thr Cys Tyr His  Ile Val Glu His Ser  Trp Phe Glu Thr Phe
                1200                1205                1210 atc atc ttc atg atc  cta ctc agc agt gga  gcg ctg gcc ttc gag       3825
Ile Ile Phe Met Ile  Leu Leu Ser Ser Gly  Ala Leu Ala Phe Glu
                1215                1220                1225 gac atc tac cta gag  gag cgg aag acc atc  aag gtt ctg ctt gag       3870
Asp Ile Tyr Leu Glu  Glu Arg Lys Thr Ile  Lys Val Leu Leu Glu
                1230                1235                1240 tat gcc gac aag atg  ttc aca tat gtc ttc  gtg ctg gag atg ctg       3915
Tyr Ala Asp Lys Met  Phe Thr Tyr Val Phe  Val Leu Glu Met Leu
                1245                1250                1255 ctc aag tgg gtg gcc  tac ggc ttc aag aag  tac ttc acc aat gcc       3960
Leu Lys Trp Val Ala  Tyr Gly Phe Lys Lys  Tyr Phe Thr Asn Ala
                1260                1265                1270 tgg tgc tgg ctc gac  ttc ctc atc gta gac  gtc tct ctg gtc agc       4005
Trp Cys Trp Leu Asp  Phe Leu Ile Val Asp  Val Ser Leu Val Ser
                1275                1280                1285 ctg gtg gcc aac acc  ctg ggc ttt gcc gag  atg ggc ccc atc aag       4050
Leu Val Ala Asn Thr  Leu Gly Phe Ala Glu  Met Gly Pro Ile Lys
                1290                1295                1300 tca ctg cgg acg ctg  cgt gca ctc cgt cct  ctg aga gct ctg tca       4095
Ser Leu Arg Thr Leu  Arg Ala Leu Arg Pro  Leu Arg Ala Leu Ser
                1305                1310                1315 cga ttt gag ggc atg  agg gtg gtg gtc aat  gcc ctg gtg ggc gcc       4140
Arg Phe Glu Gly Met  Arg Val Val Val Asn  Ala Leu Val Gly Ala
                1320                1325                1330 atc ccg tcc atc atg  aac gtc ctc ctc gtc  tgc ctc atc ttc tgg       4185
Ile Pro Ser Ile Met  Asn Val Leu Leu Val  Cys Leu Ile Phe Trp
                1335                1340                1345 ctc atc ttc agc atc  atg ggc gtg aac ctc  ttt gcg ggg aag ttt       4230
Leu Ile Phe Ser Ile  Met Gly Val Asn Leu  Phe Ala Gly Lys Phe
                1350                1355                1360 ggg agg tgc atc aac  cag aca gag gga gac  ttg cct ttg aac tac       4275
Gly Arg Cys Ile Asn  Gln Thr Glu Gly Asp  Leu Pro Leu Asn Tyr
                1365                1370                1375 acc atc gtg aac aac  aag agc cag tgt gag  tcc ttg aac ttg acc       4320
Thr Ile Val Asn Asn  Lys Ser Gln Cys Glu  Ser Leu Asn Leu Thr
                1380                1385                1390 gga gaa ttg tac tgg  acc aag gtg aaa gtc  aac ttt gac aac gtg       4365
Gly Glu Leu Tyr Trp  Thr Lys Val Lys Val  Asn Phe Asp Asn Val
                1395                1400                1405 ggg gcc ggg tac ctg  gcc ctt ctg cag gtg  gca aca ttt aaa ggc       4410
Gly Ala Gly Tyr Leu  Ala Leu Leu Gln Val  Ala Thr Phe Lys Gly
                1410                1415                1420 tgg atg gac att atg  tat gca gct gtg gac  tcc agg ggg tat gaa       4455
Trp Met Asp Ile Met  Tyr Ala Ala Val Asp  Ser Arg Gly Tyr Glu
                1425                1430                1435 gag cag cct cag tgg  gaa tac aac ctc tac  atg tac atc tat ttt       4500
Glu Gln Pro Gln Trp  Glu Tyr Asn Leu Tyr  Met Tyr Ile Tyr Phe
                1440                1445                1450 gtc att ttc atc atc  ttt ggg tct ttc ttc  acc ctg aac ctc ttt       4545
```

```
Val Ile Phe Ile Ile  Phe Gly Ser Phe Phe  Thr Leu Asn Leu Phe
            1455                 1460                 1465 att ggt gtc atc att  gac aac ttc aac caa  cag aag aaa aag tta     4590
Ile Gly Val Ile Ile  Asp Asn Phe Asn Gln  Gln Lys Lys Lys Leu
            1470                 1475                 1480 ggg ggc cag gac atc  ttc atg aca gag gag  cag aag aag tac tac     4635
Gly Gly Gln Asp Ile  Phe Met Thr Glu Glu  Gln Lys Lys Tyr Tyr
            1485                 1490                 1495 aat gcc atg aag aag  ctg ggc tcc aag aag  ccc cag aag ccc atc     4680
Asn Ala Met Lys Lys  Leu Gly Ser Lys Lys  Pro Gln Lys Pro Ile
            1500                 1505                 1510 cca cgg ccc ctg aac  aag tac cag ggc ttc  ata ttc gac att gtg     4725
Pro Arg Pro Leu Asn  Lys Tyr Gln Gly Phe  Ile Phe Asp Ile Val
            1515                 1520                 1525 acc aag cag gcc ttt  gac gtc acc atc atg  ttt ctg atc tgc ttg     4770
Thr Lys Gln Ala Phe  Asp Val Thr Ile Met  Phe Leu Ile Cys Leu
            1530                 1535                 1540 aat atg gtg acc atg  atg gtg gag aca gat  gac caa agt cct gag     4815
Asn Met Val Thr Met  Met Val Glu Thr Asp  Asp Gln Ser Pro Glu
            1545                 1550                 1555 aaa atc aac atc ttg  gcc aag atc aac ctg  ctc ttt gtg gcc atc     4860
Lys Ile Asn Ile Leu  Ala Lys Ile Asn Leu  Leu Phe Val Ala Ile
            1560                 1565                 1570 ttc aca ggc gag tgt  att gtc aag ctg gct  gcc ctg cgc cac tac     4905
Phe Thr Gly Glu Cys  Ile Val Lys Leu Ala  Ala Leu Arg His Tyr
            1575                 1580                 1585 tac ttc acc aac agc  tgg aat atc ttc gac  ttc gtg gtt gtc atc     4950
Tyr Phe Thr Asn Ser  Trp Asn Ile Phe Asp  Phe Val Val Val Ile
            1590                 1595                 1600 ctc tcc atc gtg ggc  act gtg ctc tcg gac  atc atc cag aag tac     4995
Leu Ser Ile Val Gly  Thr Val Leu Ser Asp  Ile Ile Gln Lys Tyr
            1605                 1610                 1615 ttc ttc tcc ccg acg  ctc ttc cga gtc atc  cgc ctg gcc cga ata     5040
Phe Phe Ser Pro Thr  Leu Phe Arg Val Ile  Arg Leu Ala Arg Ile
            1620                 1625                 1630 ggc cgc atc ctc aga  ctg atc cga ggg gcc  aag ggg atc cgc acg     5085
Gly Arg Ile Leu Arg  Leu Ile Arg Gly Ala  Lys Gly Ile Arg Thr
            1635                 1640                 1645 ctg ctc ttt gcc ctc  atg atg tcc ctg cct  gcc ctc ttc aac atc     5130
Leu Leu Phe Ala Leu  Met Met Ser Leu Pro  Ala Leu Phe Asn Ile
            1650                 1655                 1660 ggg ctg ctg ctc ttc  ctc gtc atg ttc atc  tac tcc atc ttt ggc     5175
Gly Leu Leu Leu Phe  Leu Val Met Phe Ile  Tyr Ser Ile Phe Gly
            1665                 1670                 1675 atg gcc aac ttc gct  tat gtc aag tgg gag  gct ggc atc gac gac     5220
Met Ala Asn Phe Ala  Tyr Val Lys Trp Glu  Ala Gly Ile Asp Asp
            1680                 1685                 1690 atg ttc aac ttc cag  acc ttc gcc aac agc  atg ctg tgc ctc ttc     5265
Met Phe Asn Phe Gln  Thr Phe Ala Asn Ser  Met Leu Cys Leu Phe
            1695                 1700                 1705 cag atc acc acg tcg  gcc ggc tgg gat ggc  ctc ctc agc ccc atc     5310
Gln Ile Thr Thr Ser  Ala Gly Trp Asp Gly  Leu Leu Ser Pro Ile
            1710                 1715                 1720 ctc aac act ggg ccg  ccc tac tgc gac ccc  act ctg ccc aac agc     5355
Leu Asn Thr Gly Pro  Pro Tyr Cys Asp Pro  Thr Leu Pro Asn Ser
            1725                 1730                 1735 aat ggc tct cgg ggg  gac tgc ggg agc cca  gcc gtg ggc atc ctc     5400
Asn Gly Ser Arg Gly  Asp Cys Gly Ser Pro  Ala Val Gly Ile Leu
            1740                 1745                 1750
```

```
ttc ttc acc acc tac  atc atc atc tcc  ttc ctc atc gtg  gtc aac         5445
Phe Phe Thr Thr Tyr  Ile Ile Ile Ser  Phe Leu Ile Val  Val Asn
            1755                1760                       1765 atg tac att gcc atc  atc ctg gag aac  ttc agc gtg gcc  acg gag         5490
Met Tyr Ile Ala Ile  Ile Leu Glu Asn  Phe Ser Val Ala  Thr Glu
            1770                1775                       1780 gag agc acc gag ccc  ctg agt gag gac  gac ttc gat atg  ttc tat         5535
Glu Ser Thr Glu Pro  Leu Ser Glu Asp  Asp Phe Asp Met  Phe Tyr
            1785                1790                       1795 gag atc tgg gag aaa  ttt gac cca gag  gcc act cag ttt  att gag         5580
Glu Ile Trp Glu Lys  Phe Asp Pro Glu  Ala Thr Gln Phe  Ile Glu
            1800                1805                       1810 tat tcg gtc ctg tct  gac ttt gcc gac  gcc ctg tct gag  cca ctc         5625
Tyr Ser Val Leu Ser  Asp Phe Ala Asp  Ala Leu Ser Glu  Pro Leu
            1815                1820                       1825 cgt atc gcc aag ccc  aac cag ata agc  ctc atc aac atg  gac ctg         5670
Arg Ile Ala Lys Pro  Asn Gln Ile Ser  Leu Ile Asn Met  Asp Leu
            1830                1835                       1840 ccc atg gtg agt ggg  gac cgc atc cat  tgc atg gac att  ctc ttt         5715
Pro Met Val Ser Gly  Asp Arg Ile His  Cys Met Asp Ile  Leu Phe
            1845                1850                       1855 gcc ttc acc aaa agg  gtc ctg ggg gag  tct ggg gag atg  gac gcc         5760
Ala Phe Thr Lys Arg  Val Leu Gly Glu  Ser Gly Glu Met  Asp Ala
            1860                1865                       1870 ctg aag atc cag atg  gag gag aag ttc  atg gca gcc aac  cca tcc         5805
Leu Lys Ile Gln Met  Glu Glu Lys Phe  Met Ala Ala Asn  Pro Ser
            1875                1880                       1885 aag atc tcc tac gag  ccc atc acc acc  aca ctc cgg cgc  aag cac         5850
Lys Ile Ser Tyr Glu  Pro Ile Thr Thr  Thr Leu Arg Arg  Lys His
            1890                1895                       1900 gaa gag gtg tcg gcc  atg gtt atc cag  aga gcc ttc cgc  agg cac         5895
Glu Glu Val Ser Ala  Met Val Ile Gln  Arg Ala Phe Arg  Arg His
            1905                1910                       1915 ctg ctg caa cgc tct  ttg aag cat gcc  tcc ttc ctc ttc  cgt cag         5940
Leu Leu Gln Arg Ser  Leu Lys His Ala  Ser Phe Leu Phe  Arg Gln
            1920                1925                       1930 cag gcg ggc agc ggc  ctc tcc gaa gag  gat gcc cct gag  cga gag         5985
Gln Ala Gly Ser Gly  Leu Ser Glu Glu  Asp Ala Pro Glu  Arg Glu
            1935                1940                       1945 ggc ctc atc gcc tac  gtg atg agt gag  aac ttc tcc cga  ccc ctt         6030
Gly Leu Ile Ala Tyr  Val Met Ser Glu  Asn Phe Ser Arg  Pro Leu
            1950                1955                       1960 ggc cca ccc tcc agc  tcc tcc atc tcc  tcc act tcc ttc  cca ccc         6075
Gly Pro Pro Ser Ser  Ser Ser Ile Ser  Ser Thr Ser Phe  Pro Pro
            1965                1970                       1975 tcc tat gac agt gtc  act aga gcc acc  agc gat aac ctc  cag gtg         6120
Ser Tyr Asp Ser Val  Thr Arg Ala Thr  Ser Asp Asn Leu  Gln Val
            1980                1985                       1990 cgg ggg tct gac tac  agc cac agt gaa  gat ctc gcc gac  ttc ccc         6165
Arg Gly Ser Asp Tyr  Ser His Ser Glu  Asp Leu Ala Asp  Phe Pro
            1995                2000                       2005 cct tct ccg gac agg  gac cgt gag tcc  atc gtg tgagcctcgg               6208
Pro Ser Pro Asp Arg  Asp Arg Glu Ser  Ile Val
            2010                2015 cctggctggc caggacacac tgaaaagcag ccttttttcac catggcaaac ctaaatgcag     6268
tcagtcacaa accagcctgg ggccttcctg gctttgggag taagaaatgg gcctcggccc     6328
cgcggatcaa ccaggcagag ttctgtggcg ccgcgtggac agccggagca gttggcctgt     6388
gcttggaggc ctcagataga cctgtgacct ggtctggtca ggcaatgccc ctgcggctct     6448
```

```
ggaaagcaac ttcatcccag ctgctgaggc gaaatataaa actgagactg tatatgttgt    6508
gaatgggctt tcataaattt attatatttg atatttttt acttgagcaa agaactaagg    6568 attttccat ggacatgggc agcaattcac gctgtctctt cttaaccctg aacaagagtg    6628
tctatggagc agccggaagt ctgttctcaa agcagaagtg aatccagtg tggctcccac     6688 aggtcttcac tgcccagggg tcgaatgggg tccccctccc acttgacctg agatgctggg    6748
agggctgaac ccccactcac acaagcacac acacacacag tcctcacaca cggaggccag    6808
acacaggccg tgggacccag gctcccagcc taagggagac aggcctttcc ctgccggccc    6868
cccaaggatg gggttcttgt ccacggggct cactctggcc ccctattgtc tcccaaggtc    6928
ccattttccc ccttgtgttt tcacgcaggt catattgtca gtcctacaaa aataaaaggc    6988
ttccagagga gagtggcctg gggtcccagg gctgggccnt aggcactgat agttgccttt    7048
tcttcccctc ctgtaagagt attaacaaaa ccaaaggaca caaggtgca agccccattc     7108 acggcctggc atgcagcttg tccttgctcc tggaacctgg caggccctgc cagccagcca    7168
atggaagaga ggggctgagc catgggggtt tggggctaag aagttcacca gccctgagcc    7228
atggsnsccc tcagcctgcc tgaagagagg aaactggcga tctcccaggg ctctctggac    7288
catacncgga ggagttttcn ngtgtggtct ccagctcctc tccagacaca gagacatggg    7348
agtggggagc ggacgttggc cctggccctg tgcagggaaa gggatggtca ggcccagttc    7408
tcgtgcccct tagaggggaa tgaaccatgg caccttgag agagggggca ctgtggtcag    7468
gcccagcctc tctggcnnag tcccgggatc ctgatgcac ccacacagag gacctctttg     7528
gggcaagatc caggtggntc ccataggtct tgtgaaaagg cttttcagg gaaaaatatt    7588 ttactagtcc aatcacccc aggacctctt cagctgctga caatcctatt tagcatatgc     7648
aaatctttta acatagagaa ctgtcaccct gaggtaacag ggtcaactgg cgaagagcag    7708 gccaggggc ttggctgnnc cattccagct ctnccacnga nnnctccwm ncnnnnncat     7768 nnctcccagg ccacctcagt ctcanctgcc ggctctgggc tggctnctcc taacctacct    7828
nnccgagctg tcggagggct ggacatttgt ggcagtgctg aangggcat tgsnggcgag     7888 taaagtatta kgtttcttct tgtcacccca gttcccttgg tggcaacccc agcccaacc    7948 catgcccctg acagatctag ttctcttcts ctgtgttccc tttgagtccn gtgtgggaca    8008
cggtttaact gtcccagcga gattctccca agtngaaatc ctatttttgt agatctccat    8068
gctttgnctc tcaaggcttg gagaggtatg tgcccctcct nggbnctcac cgcctgctac    8128
acaggcagga atgcggnttg ggaggcaggt cgggctssna gcccagctgg ccggaaggag    8188
actgtggttt ttgtgtgtgt ggacagcncg ggagctttga gacaggntgc ctggggctgg    8248
ctgcagacgg tgtggttggg ggtgggaggt gagctagacc nnnccttag cttttagcct     8308 ggctgtcacc tttttaattt ccagaactgc acaatgacca gnaggagggg agaagagagt    8368
aggaaaaagg agggaaggac agacatcaag tgccagatgt tgtctgaact aatcgagcac    8428
ttctcaccaa acttcnngta taaataaaat acatannnng gggcaaacca ataaatggct    8488
tac                                                                 8491
```

<210> SEQ ID NO 4
<211> LENGTH: 2016
<212> TYPE: PRT
<213> ORGANISM: Homo sapiens
<220> FEATURE:
<221> NAME/KEY: misc_feature
<222> LOCATION: (1)..(8491)

<223> OTHER INFORMATION: n may be any base

<400> SEQUENCE: 4

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Val Arg Arg Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Ala Phe Cys Leu His Ala Phe Thr Phe Leu Arg Asp Pro
            180                 185                 190

Trp Asn Trp Leu Asp Phe Ser Val Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270

Met Gly Asn Leu Arg His Lys Cys Val Arg Asn Phe Thr Ala Leu Asn
        275                 280                 285

Gly Thr Asn Gly Ser Val Glu Ala Asp Gly Leu Val Trp Glu Ser Leu
    290                 295                 300

Asp Leu Tyr Leu Ser Asp Pro Glu Asn Tyr Leu Leu Lys Asn Gly Thr
305                 310                 315                 320

Ser Asp Val Leu Leu Cys Gly Asn Ser Ser Asp Ala Gly Thr Cys Pro
                325                 330                 335

Glu Gly Tyr Arg Cys Leu Lys Ala Gly Glu Asn Pro Asp His Gly Tyr
            340                 345                 350

Thr Ser Phe Asp Ser Phe Ala Trp Ala Phe Leu Ala Leu Phe Arg Leu
        355                 360                 365

Met Thr Gln Asp Cys Trp Glu Arg Leu Tyr Gln Gln Thr Leu Arg Ser
    370                 375                 380

Ala Gly Lys Ile Tyr Met Ile Phe Phe Met Leu Val Ile Phe Leu Gly
385                 390                 395                 400
```

-continued

```
Ser Phe Tyr Leu Val Asn Leu Ile Leu Ala Val Val Met Ala Tyr
            405                 410                 415

Glu Glu Gln Asn Gln Ala Thr Ile Ala Glu Thr Glu Lys Glu Lys
            420                 425                 430

Arg Phe Gln Glu Ala Met Glu Met Leu Lys Lys Glu His Glu Ala Leu
            435                 440                 445

Thr Ile Arg Gly Val Asp Thr Val Ser Arg Ser Ser Leu Glu Met Ser
            450                 455                 460

Pro Leu Ala Pro Val Asn Ser His Glu Arg Arg Ser Lys Arg Arg Lys
465                 470                 475                 480

Arg Met Ser Ser Gly Thr Glu Glu Cys Gly Glu Asp Arg Leu Pro Lys
                485                 490                 495

Ser Asp Ser Glu Asp Gly Pro Arg Ala Met Asn His Leu Ser Leu Thr
                500                 505                 510

Arg Gly Leu Ser Arg Thr Ser Met Lys Pro Arg Ser Ser Arg Gly Ser
            515                 520                 525

Ile Phe Thr Phe Arg Arg Arg Asp Leu Gly Ser Glu Ala Asp Phe Ala
            530                 535                 540

Asp Asp Glu Asn Ser Thr Ala Arg Glu Ser Glu Ser His His Thr Ser
545                 550                 555                 560

Leu Leu Val Pro Trp Pro Leu Arg Arg Thr Ser Ala Gln Gly Gln Pro
                565                 570                 575

Ser Pro Gly Thr Ser Ala Pro Gly His Ala Leu His Gly Lys Lys Asn
            580                 585                 590

Ser Thr Val Asp Cys Asn Gly Val Val Ser Leu Leu Gly Ala Gly Asp
            595                 600                 605

Pro Glu Ala Thr Ser Pro Gly Ser His Leu Leu Arg Pro Val Met Leu
            610                 615                 620

Glu His Pro Pro Asp Thr Thr Thr Pro Ser Glu Glu Pro Gly Gly Pro
625                 630                 635                 640

Gln Met Leu Thr Ser Gln Ala Pro Cys Val Asp Gly Phe Glu Glu Pro
                645                 650                 655

Gly Ala Arg Gln Arg Ala Leu Ser Ala Val Ser Val Leu Thr Ser Ala
                660                 665                 670

Leu Glu Glu Leu Glu Glu Ser Arg His Lys Cys Pro Pro Cys Trp Asn
            675                 680                 685

Arg Leu Ala Gln Arg Tyr Leu Ile Trp Glu Cys Cys Pro Leu Trp Met
690                 695                 700

Ser Ile Lys Gln Gly Val Lys Leu Val Val Met Asp Pro Phe Thr Asp
705                 710                 715                 720

Leu Thr Ile Thr Met Cys Ile Val Leu Asn Thr Leu Phe Met Ala Leu
                725                 730                 735

Glu His Tyr Asn Met Thr Ser Glu Phe Glu Glu Met Leu Gln Val Gly
            740                 745                 750

Asn Leu Val Phe Thr Gly Ile Phe Thr Ala Glu Met Thr Phe Lys Ile
            755                 760                 765

Ile Ala Leu Asp Pro Tyr Tyr Tyr Phe Gln Gln Gly Trp Asn Ile Phe
            770                 775                 780

Asp Ser Ile Ile Val Ile Leu Ser Leu Met Glu Leu Gly Leu Ser Arg
785                 790                 795                 800

Met Ser Asn Leu Ser Val Leu Arg Ser Phe Arg Leu Leu Arg Val Phe
                805                 810                 815

Lys Leu Ala Lys Ser Trp Pro Thr Leu Asn Thr Leu Ile Lys Ile Ile
```

-continued

```
                820                 825                 830
Gly Asn Ser Val Gly Ala Leu Gly Asn Leu Thr Leu Val Leu Ala Ile
            835                 840                 845
Ile Val Phe Ile Phe Ala Val Val Gly Met Gln Leu Phe Gly Lys Asn
        850                 855                 860
Tyr Ser Glu Leu Arg Asp Ser Asp Ser Gly Leu Leu Pro Arg Trp His
865                 870                 875                 880
Met Met Asp Phe Phe His Ala Phe Leu Ile Ile Phe Arg Ile Leu Cys
                885                 890                 895
Gly Glu Trp Ile Glu Thr Met Trp Asp Cys Met Glu Val Ser Gly Gln
            900                 905                 910
Ser Leu Cys Leu Leu Val Phe Leu Leu Val Met Val Ile Gly Asn Leu
        915                 920                 925
Val Val Leu Asn Leu Phe Leu Ala Leu Leu Leu Ser Ser Phe Ser Ala
        930                 935                 940
Asp Asn Leu Thr Ala Pro Asp Glu Asp Arg Glu Met Asn Asn Leu Gln
945                 950                 955                 960
Leu Ala Leu Ala Arg Ile Gln Arg Gly Leu Arg Phe Val Lys Arg Thr
                965                 970                 975
Thr Trp Asp Phe Cys Cys Gly Leu Leu Arg His Arg Pro Gln Lys Pro
            980                 985                 990
Ala Ala Leu Ala Ala Gln Gly Gln  Leu Pro Ser Cys Ile  Ala Thr Pro
        995                 1000                1005
Tyr Ser  Pro Pro Pro Pro Glu  Thr Glu Lys Val Pro  Pro Thr Arg
    1010                1015                1020
Lys Glu  Thr Gln Phe Glu Glu  Gly Glu Gln Pro Gly  Gln Gly Thr
    1025                1030                1035
Pro Gly  Asp Pro Glu Pro Val  Cys Val Pro Ile Ala  Val Ala Glu
    1040                1045                1050
Ser Asp  Thr Asp Asp Gln Glu  Glu Asp Glu Glu Asn  Ser Leu Gly
    1055                1060                1065
Thr Glu  Glu Glu Ser Ser Lys  Gln Gln Glu Ser Gln  Pro Val Ser
    1070                1075                1080
Gly Trp  Pro Arg Gly Pro Pro  Asp Ser Arg Thr Trp  Ser Gln Val
    1085                1090                1095
Ser Ala  Thr Ala Tyr Ser Glu  Ala Glu Ala Ser Ala  Ser Gln Ala
    1100                1105                1110
Asp Trp  Arg Gln Gln Trp Lys  Ala Glu Pro Gln Ala  Pro Gly Cys
    1115                1120                1125
Gly Glu  Thr Pro Glu Asp Ser  Cys Ser Glu Gly Ser  Thr Ala Asp
    1130                1135                1140
Met Thr  Asn Thr Ala Glu Leu  Leu Glu Gln Ile Pro  Asp Leu Gly
    1145                1150                1155
Gln Asp  Val Lys Asp Pro Glu  Asp Cys Phe Thr Glu  Gly Cys Val
    1160                1165                1170
Arg Arg  Cys Pro Cys Cys Ala  Val Asp Thr Thr Gln  Ala Pro Gly
    1175                1180                1185
Lys Val  Trp Trp Arg Leu Arg  Lys Thr Cys Tyr His  Ile Val Glu
    1190                1195                1200
His Ser  Trp Phe Glu Thr Phe  Ile Ile Phe Met Ile  Leu Leu Ser
    1205                1210                1215
Ser Gly  Ala Leu Ala Phe Glu  Asp Ile Tyr Leu Glu  Glu Arg Lys
    1220                1225                1230
```

-continued

```
Thr Ile Lys Val Leu Leu Glu Tyr Ala Asp Lys Met Phe Thr Tyr
1235                1240                1245

Val Phe Val Leu Glu Met Leu Leu Lys Trp Val Ala Tyr Gly Phe
1250                1255                1260

Lys Lys Tyr Phe Thr Asn Ala Trp Cys Trp Leu Asp Phe Leu Ile
1265                1270                1275

Val Asp Val Ser Leu Val Ser Leu Val Ala Asn Thr Leu Gly Phe
1280                1285                1290

Ala Glu Met Gly Pro Ile Lys Ser Leu Arg Thr Leu Arg Ala Leu
1295                1300                1305

Arg Pro Leu Arg Ala Leu Ser Arg Phe Glu Gly Met Arg Val Val
1310                1315                1320

Val Asn Ala Leu Val Gly Ala Ile Pro Ser Ile Met Asn Val Leu
1325                1330                1335

Leu Val Cys Leu Ile Phe Trp Leu Ile Phe Ser Ile Met Gly Val
1340                1345                1350

Asn Leu Phe Ala Gly Lys Phe Gly Arg Cys Ile Asn Gln Thr Glu
1355                1360                1365

Gly Asp Leu Pro Leu Asn Tyr Thr Ile Val Asn Asn Lys Ser Gln
1370                1375                1380

Cys Glu Ser Leu Asn Leu Thr Gly Glu Leu Tyr Trp Thr Lys Val
1385                1390                1395

Lys Val Asn Phe Asp Asn Val Gly Ala Gly Tyr Leu Ala Leu Leu
1400                1405                1410

Gln Val Ala Thr Phe Lys Gly Trp Met Asp Ile Met Tyr Ala Ala
1415                1420                1425

Val Asp Ser Arg Gly Tyr Glu Glu Gln Pro Gln Trp Glu Tyr Asn
1430                1435                1440

Leu Tyr Met Tyr Ile Tyr Phe Val Ile Phe Ile Ile Phe Gly Ser
1445                1450                1455

Phe Phe Thr Leu Asn Leu Phe Ile Gly Val Ile Ile Asp Asn Phe
1460                1465                1470

Asn Gln Gln Lys Lys Lys Leu Gly Gly Gln Asp Ile Phe Met Thr
1475                1480                1485

Glu Glu Gln Lys Lys Tyr Tyr Asn Ala Met Lys Lys Leu Gly Ser
1490                1495                1500

Lys Lys Pro Gln Lys Pro Ile Pro Arg Pro Leu Asn Lys Tyr Gln
1505                1510                1515

Gly Phe Ile Phe Asp Ile Val Thr Lys Gln Ala Phe Asp Val Thr
1520                1525                1530

Ile Met Phe Leu Ile Cys Leu Asn Met Val Thr Met Met Val Glu
1535                1540                1545

Thr Asp Asp Gln Ser Pro Glu Lys Ile Asn Ile Leu Ala Lys Ile
1550                1555                1560

Asn Leu Leu Phe Val Ala Ile Phe Thr Gly Glu Cys Ile Val Lys
1565                1570                1575

Leu Ala Ala Leu Arg His Tyr Tyr Phe Thr Asn Ser Trp Asn Ile
1580                1585                1590

Phe Asp Phe Val Val Val Ile Leu Ser Ile Val Gly Thr Val Leu
1595                1600                1605

Ser Asp Ile Ile Gln Lys Tyr Phe Phe Ser Pro Thr Leu Phe Arg
1610                1615                1620
```

-continued

```
Val Ile Arg Leu Ala Arg Ile Gly Arg Ile Leu Arg Leu Ile Arg
    1625                1630                1635

Gly Ala Lys Gly Ile Arg Thr Leu Leu Phe Ala Leu Met Met Ser
    1640                1645                1650

Leu Pro Ala Leu Phe Asn Ile Gly Leu Leu Leu Phe Leu Val Met
    1655                1660                1665

Phe Ile Tyr Ser Ile Phe Gly Met Ala Asn Phe Ala Tyr Val Lys
    1670                1675                1680

Trp Glu Ala Gly Ile Asp Asp Met Phe Asn Phe Gln Thr Phe Ala
    1685                1690                1695

Asn Ser Met Leu Cys Leu Phe Gln Ile Thr Thr Ser Ala Gly Trp
    1700                1705                1710

Asp Gly Leu Leu Ser Pro Ile Leu Asn Thr Gly Pro Pro Tyr Cys
    1715                1720                1725

Asp Pro Thr Leu Pro Asn Ser Asn Gly Ser Arg Gly Asp Cys Gly
    1730                1735                1740

Ser Pro Ala Val Gly Ile Leu Phe Phe Thr Thr Tyr Ile Ile Ile
    1745                1750                1755

Ser Phe Leu Ile Val Val Asn Met Tyr Ile Ala Ile Ile Leu Glu
    1760                1765                1770

Asn Phe Ser Val Ala Thr Glu Glu Ser Thr Glu Pro Leu Ser Glu
    1775                1780                1785

Asp Asp Phe Asp Met Phe Tyr Glu Ile Trp Glu Lys Phe Asp Pro
    1790                1795                1800

Glu Ala Thr Gln Phe Ile Glu Tyr Ser Val Leu Ser Asp Phe Ala
    1805                1810                1815

Asp Ala Leu Ser Glu Pro Leu Arg Ile Ala Lys Pro Asn Gln Ile
    1820                1825                1830

Ser Leu Ile Asn Met Asp Leu Pro Met Val Ser Gly Asp Arg Ile
    1835                1840                1845

His Cys Met Asp Ile Leu Phe Ala Phe Thr Lys Arg Val Leu Gly
    1850                1855                1860

Glu Ser Gly Glu Met Asp Ala Leu Lys Ile Gln Met Glu Glu Lys
    1865                1870                1875

Phe Met Ala Ala Asn Pro Ser Lys Ile Ser Tyr Glu Pro Ile Thr
    1880                1885                1890

Thr Thr Leu Arg Arg Lys His Glu Glu Val Ser Ala Met Val Ile
    1895                1900                1905

Gln Arg Ala Phe Arg Arg His Leu Leu Gln Arg Ser Leu Lys His
    1910                1915                1920

Ala Ser Phe Leu Phe Arg Gln Gln Ala Gly Ser Gly Leu Ser Glu
    1925                1930                1935

Glu Asp Ala Pro Glu Arg Glu Gly Leu Ile Ala Tyr Val Met Ser
    1940                1945                1950

Glu Asn Phe Ser Arg Pro Leu Gly Pro Pro Ser Ser Ser Ser Ile
    1955                1960                1965

Ser Ser Thr Ser Phe Pro Pro Ser Tyr Asp Ser Val Thr Arg Ala
    1970                1975                1980

Thr Ser Asp Asn Leu Gln Val Arg Gly Ser Asp Tyr Ser His Ser
    1985                1990                1995

Glu Asp Leu Ala Asp Phe Pro Pro Ser Pro Asp Arg Asp Arg Glu
    2000                2005                2010

Ser Ile Val
```

```
2015

<210> SEQ ID NO 5
<211> LENGTH: 60
<212> TYPE: DNA
<213> ORGANISM: Artificial
<220> FEATURE:
<223> OTHER INFORMATION: Theoretical sequence to demonstrate percent
      homology

<400> SEQUENCE: 5
accgtagcta cgtacgtata tagaaagggc gcgatcgtcg tcgcgtatga cgacttagca      60

<210> SEQ ID NO 6
<211> LENGTH: 130
<212> TYPE: DNA
<213> ORGANISM: Artificial
<220> FEATURE:
<223> OTHER INFORMATION: Theoretical sequence to demonstrate percent
      homology

<400> SEQUENCE: 6
accggtagct acgtacgtta tttagaaagg ggtgtgtgtg tgtgtgtaaa ccggggtttt      60
cgggatcgtc cgtcgcgtat gacgacttag ccatgcacgg tatatcgtat taggactagc     120
gattgactag                                                            130
```